United States Patent
Nilsson

(10) Patent No.: US 10,456,215 B2
(45) Date of Patent: Oct. 29, 2019

(54) SYSTEM AND METHOD FOR PLANNING A FIRST AND SECOND DENTAL RESTORATION

(75) Inventor: Urban Nilsson, Halta (SE)

(73) Assignee: NOBEL BIOCARE SERVICES AG, Kloten (CH)

( * ) Notice: Subject to any disclaimer, the term of this patent is extended or adjusted under 35 U.S.C. 154(b) by 50 days.

(21) Appl. No.: 13/509,455

(22) PCT Filed: Nov. 15, 2010

(86) PCT No.: PCT/EP2010/006928
§ 371 (c)(1),
(2), (4) Date: Jul. 24, 2012

(87) PCT Pub. No.: WO2011/057809
PCT Pub. Date: May 19, 2011

(65) Prior Publication Data
US 2012/0282567 A1  Nov. 8, 2012

(30) Foreign Application Priority Data
Nov. 16, 2009 (EP) .................................. 09014293

(51) Int. Cl.
*A61C 1/08* (2006.01)
*A61C 13/00* (2006.01)
*G16H 20/40* (2018.01)

(52) U.S. Cl.
CPC .......... *A61C 1/084* (2013.01); *A61C 13/0004* (2013.01); *G16H 20/40* (2018.01)

(58) Field of Classification Search
CPC ..... A61C 13/0004; A61C 1/084; G16H 20/40
(Continued)

(56) References Cited

U.S. PATENT DOCUMENTS

| 4,663,720 A | 5/1987 | Duret et al. |
| 5,360,446 A | 11/1994 | Kennedy |

(Continued)

FOREIGN PATENT DOCUMENTS

| EP | 2254068 A1 | 11/2010 |
| EP | 2322115 A1 | 5/2011 |

(Continued)

OTHER PUBLICATIONS

International Search Report for PCT International Application No. PCT/EP2010/006929 dated Jun. 6, 2011.
(Continued)

*Primary Examiner* — Cris L. Rodriguez
*Assistant Examiner* — Hao D Mai
(74) *Attorney, Agent, or Firm* — Knobbe Martens Olson & Bear LLP

(57) ABSTRACT

A computer-based method and system of virtually planning a dental restoration in a patient are disclosed, including steps, units or code segments for virtually planning a first dental restoration. First production data is based on the planned first dental restoration for production thereof or of a product related to a medical procedure for installing at least a portion of the first dental restoration in an oral cavity of the patient. Scan data is provided including factual position data and/or factual shape data based on the first dental restoration when at least partly installed in the oral cavity of the patient. The second dental restoration is virtually planned, including adjusting the planned first dental restoration in dependence of the scan data. Second production data is provided based on the planned second dental restoration useful for production of the second dental restoration.

19 Claims, 13 Drawing Sheets

(58) Field of Classification Search
USPC .................................. 433/68, 215; 700/97–98
See application file for complete search history.

(56) References Cited

U.S. PATENT DOCUMENTS

| | | | |
|---|---|---|---|
| 5,725,376 A | 3/1998 | Poirier | |
| 5,768,134 A | 6/1998 | Swaelens et al. | |
| 5,816,810 A | 10/1998 | Antonson et al. | |
| 5,851,115 A | 12/1998 | Carlsson | |
| 5,857,853 A | 1/1999 | Van Nifterick et al. | |
| 6,319,006 B1 | 11/2001 | Scherer | |
| 6,814,575 B2 | 11/2004 | Poirier | |
| 7,153,135 B1 | 12/2006 | Thomas | |
| 7,331,786 B2 | 2/2008 | Poirier | |
| 7,925,374 B2 | 4/2011 | Andersson et al. | |
| 2004/0248066 A1* | 12/2004 | Recigno | A61C 13/00 433/213 |
| 2005/0277091 A1 | 12/2005 | Andersson et al. | |
| 2006/0040236 A1 | 2/2006 | Schmitt | |
| 2006/0127852 A1 | 6/2006 | Wen | |
| 2006/0127854 A1 | 6/2006 | Wen | |
| 2007/0190492 A1* | 8/2007 | Schmitt | A61C 13/0004 433/213 |
| 2008/0193899 A1 | 8/2008 | Karlsson et al. | |
| 2009/0148813 A1* | 6/2009 | Sun | A61C 13/0001 433/201.1 |
| 2009/0298017 A1* | 12/2009 | Boerjes | A61B 5/4547 433/214 |
| 2010/0151417 A1 | 6/2010 | Nilsson et al. | |
| 2010/0332253 A1* | 12/2010 | Adusimilli | A61C 11/00 705/2 |
| 2011/0196524 A1 | 8/2011 | Giasson et al. | |
| 2011/0276159 A1* | 11/2011 | Chun | A61C 13/0004 700/98 |
| 2012/0040311 A1 | 2/2012 | Nilsson et al. | |
| 2012/0123576 A1 | 5/2012 | Pettersson et al. | |
| 2012/0171635 A1 | 7/2012 | Karlsson et al. | |
| 2012/0179281 A1* | 7/2012 | Steingart | A61C 13/0004 700/97 |
| 2012/0183921 A1 | 7/2012 | Karlsson et al. | |

FOREIGN PATENT DOCUMENTS

| | | |
|---|---|---|
| WO | WO 2004/075771 A1 | 9/2004 |
| WO | WO 2004/098378 A2 | 11/2004 |
| WO | WO 2006/031096 A1 | 3/2006 |
| WO | WO 2007/117309 A2 | 10/2007 |
| WO | WO 2007/127804 A2 | 11/2007 |
| WO | WO 2007/134701 A1 | 11/2007 |
| WO | WO 2008/033893 A1 | 3/2008 |
| WO | WO 2008/083857 A1 | 7/2008 |
| WO | WO 2008/112925 A2 | 9/2008 |
| WO | WO 2008/145293 A2 | 12/2008 |
| WO | WO 2009/010543 A1 | 1/2009 |
| WO | WO 2009/033677 A2 | 3/2009 |

OTHER PUBLICATIONS

International Preliminary Report on Patentability for PCT International Application No. PCT/EP2010/006929 dated May 22, 2012.
International Search Report for PCT Patent Application No. PCT/EP2010/006928 dated Feb. 1, 2011.
International Preliminary Report on Patentability for PCT Patent Application No. PCT/EP2010/006928 dated May 22, 2012.

* cited by examiner

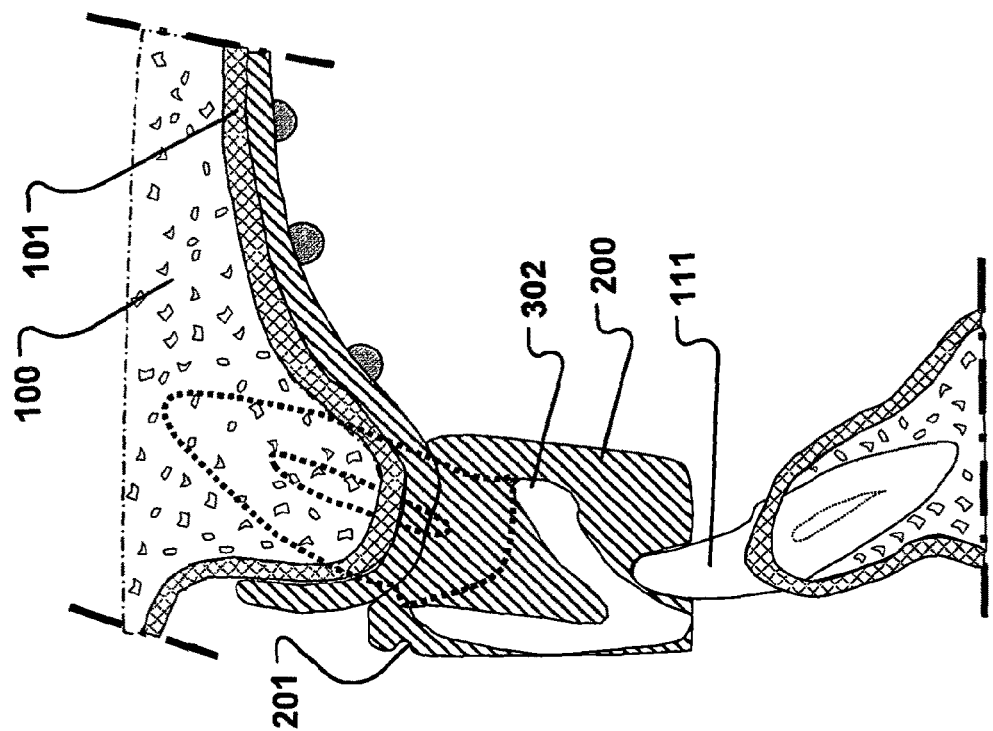
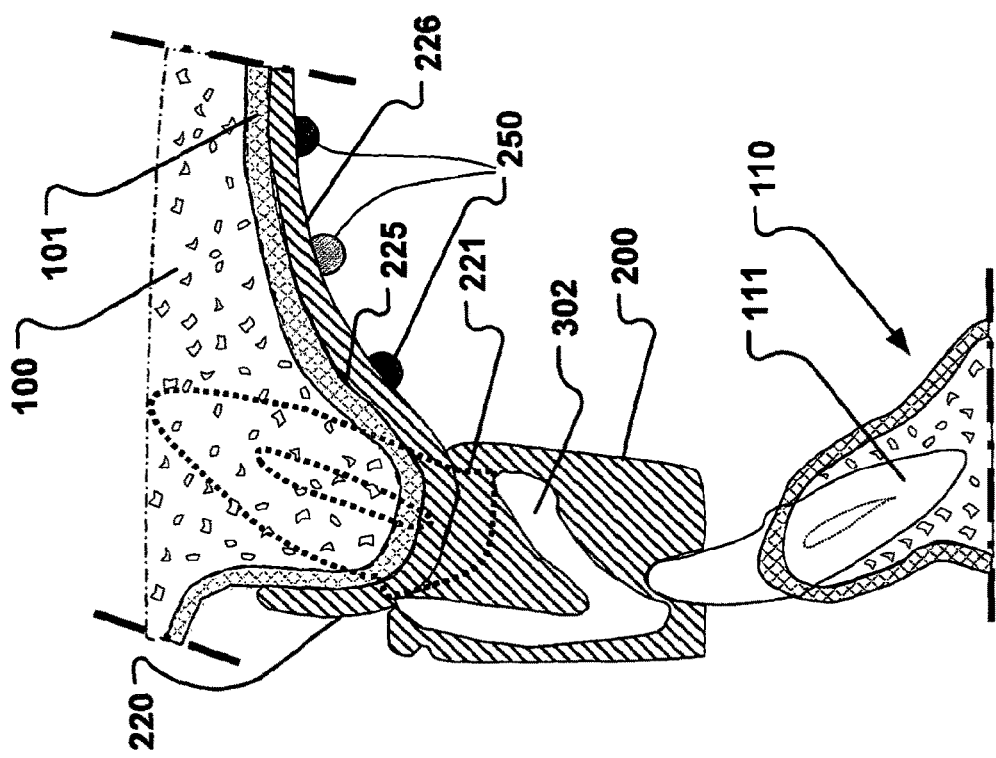

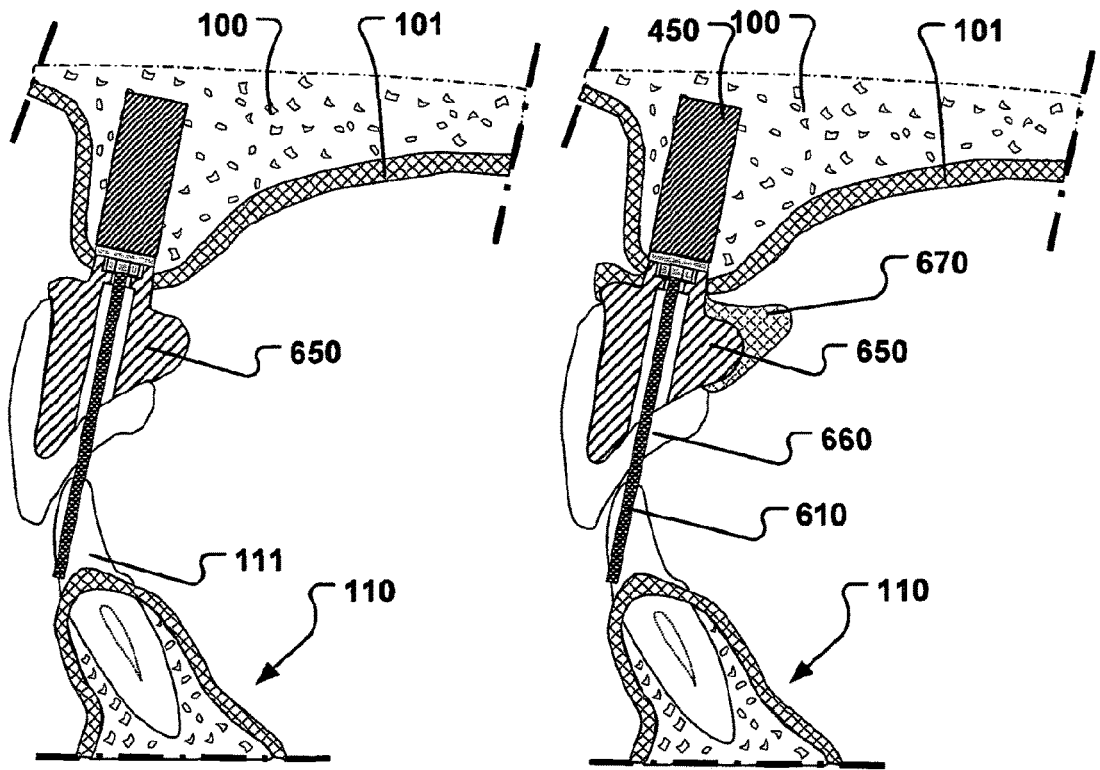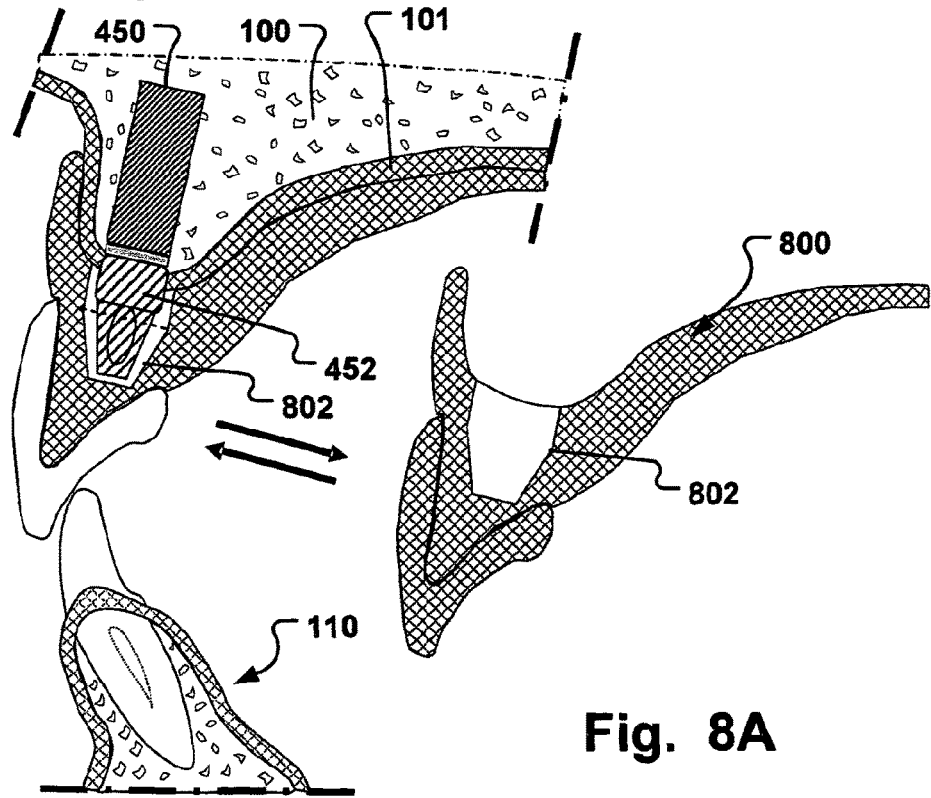

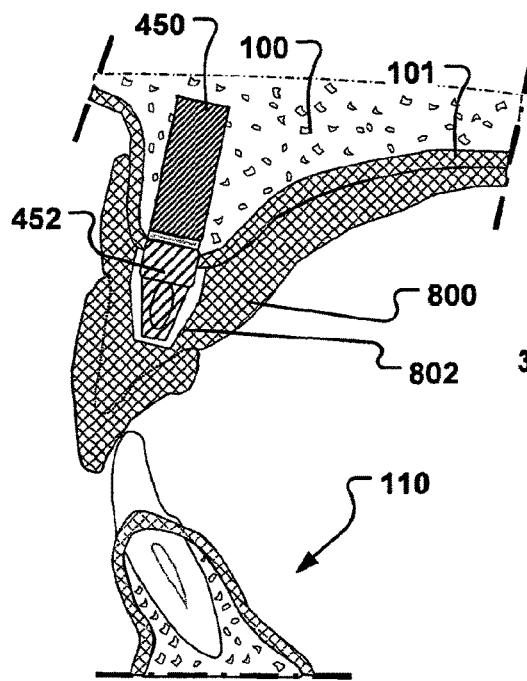
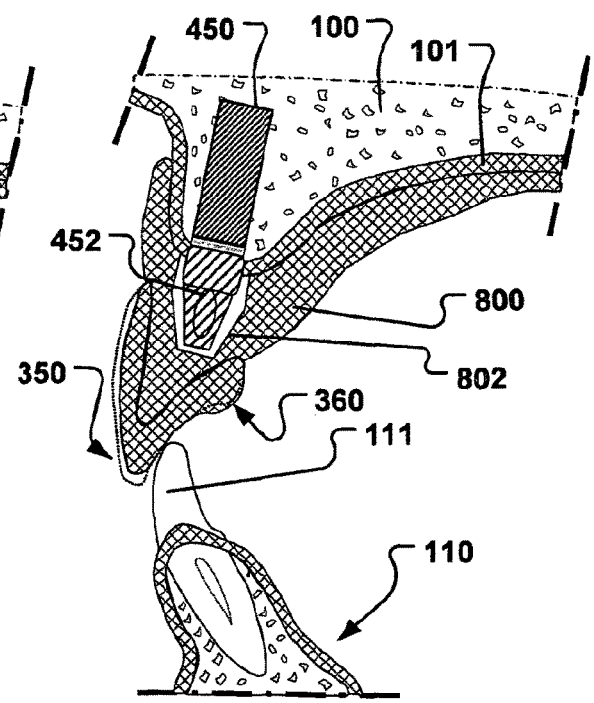
Fig. 10A　　　　Fig. 10B
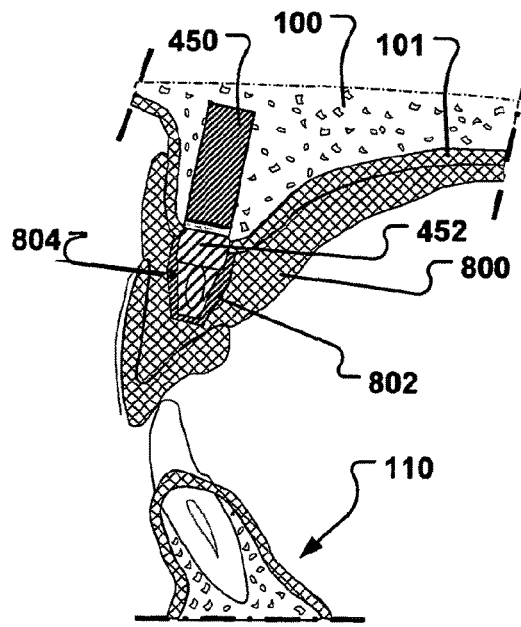
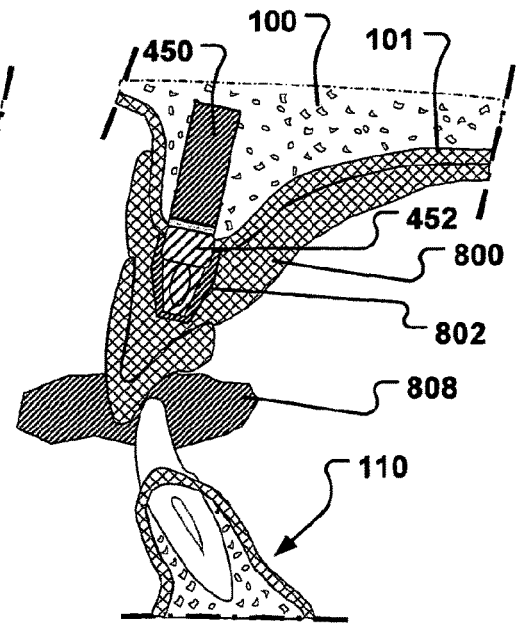
Fig. 11A　　　　Fig. 11B

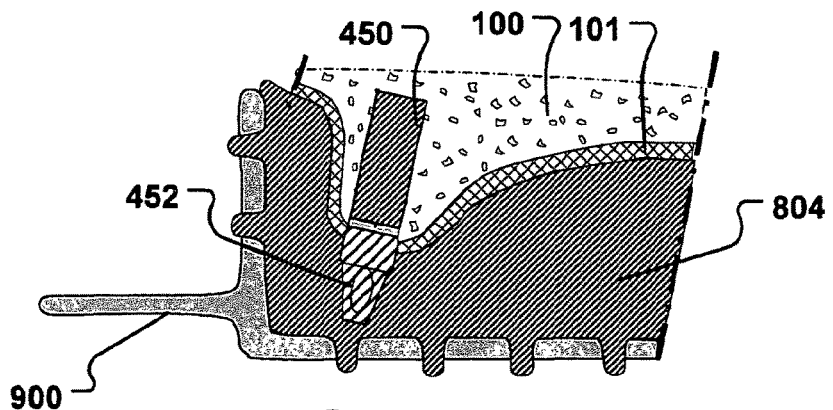
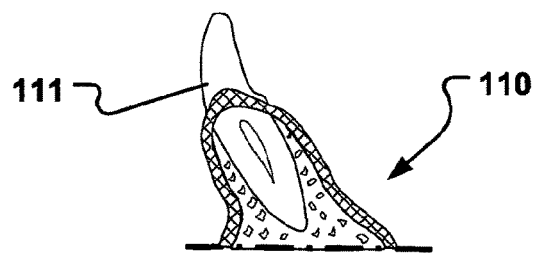
Fig. 11C
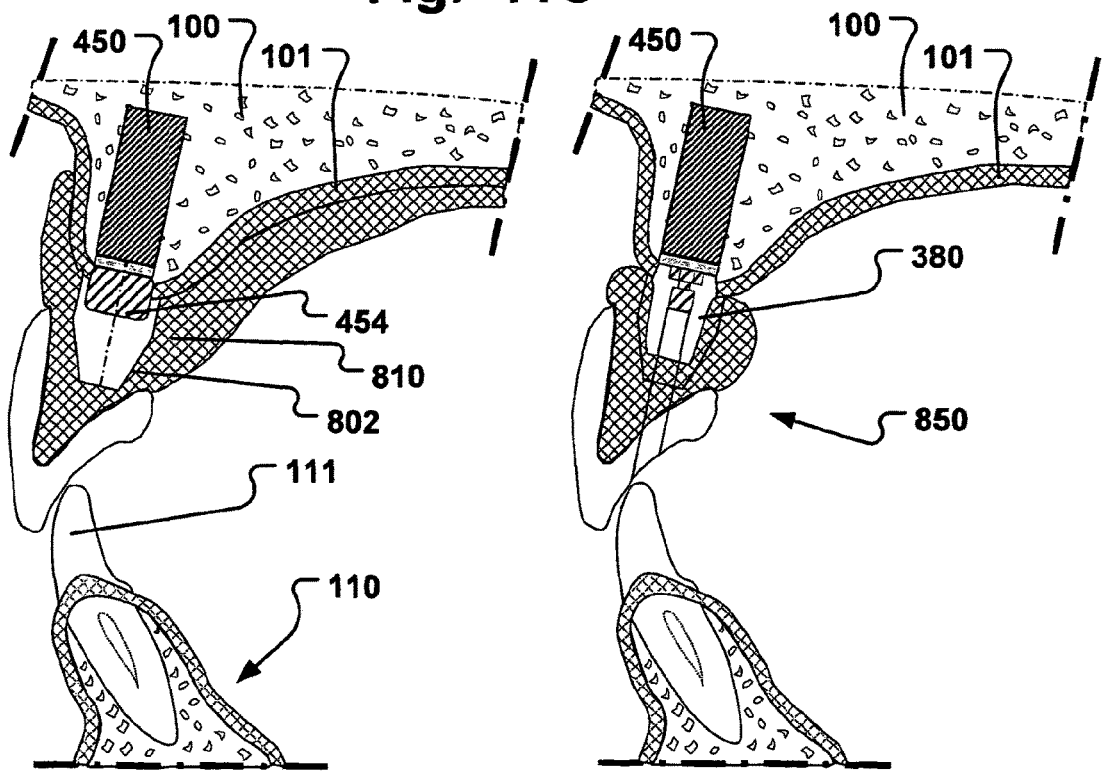
Fig. 12A        Fig. 12B

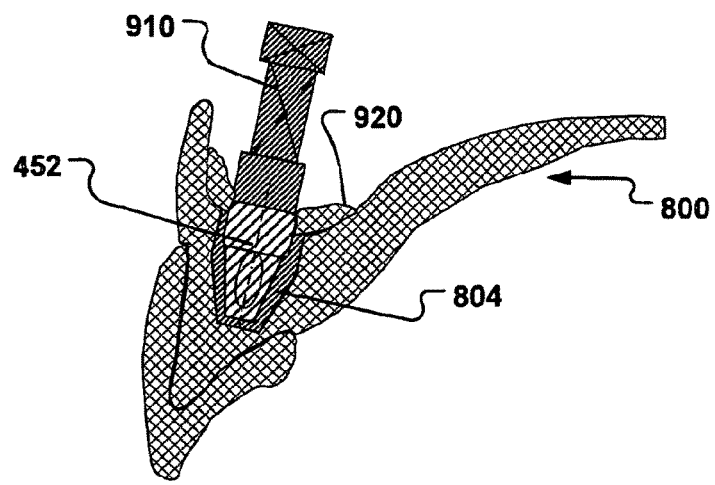
Fig. 13C
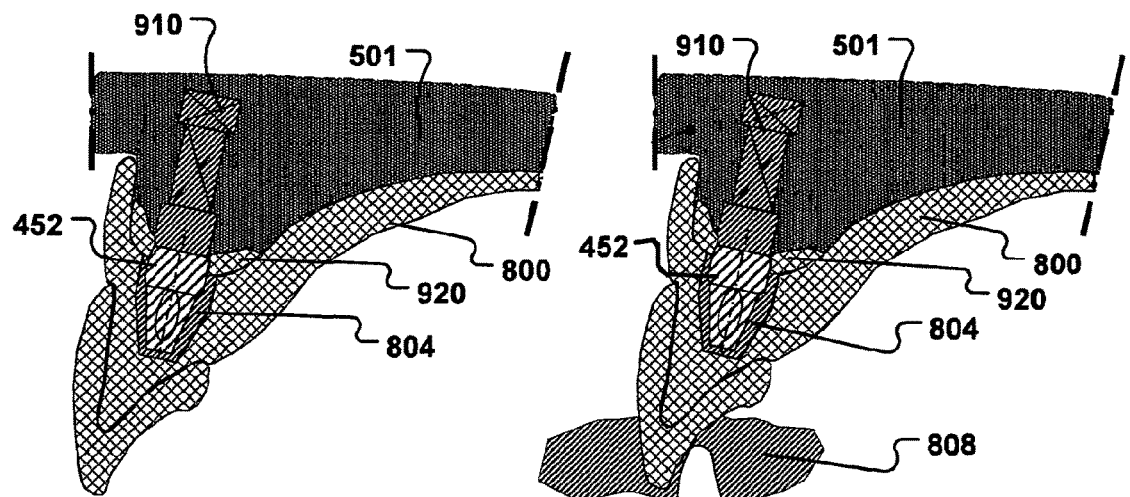
Fig. 13D
Fig. 13E

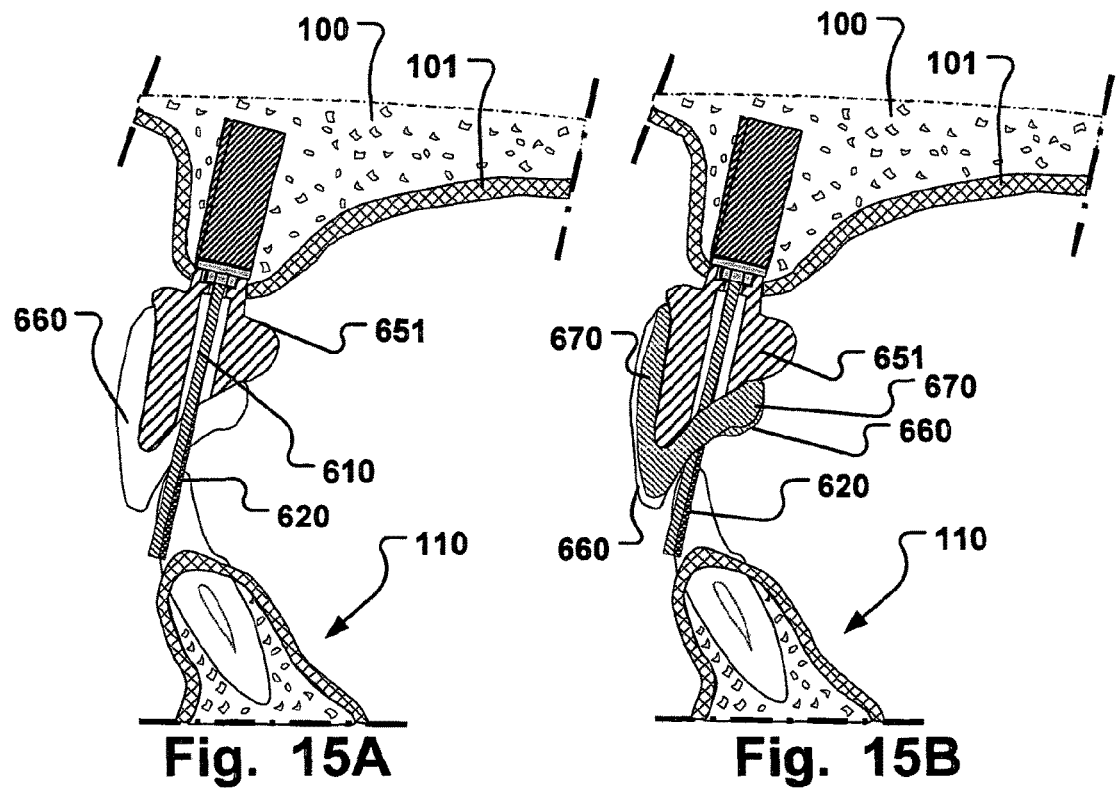
Fig. 15A
Fig. 15B
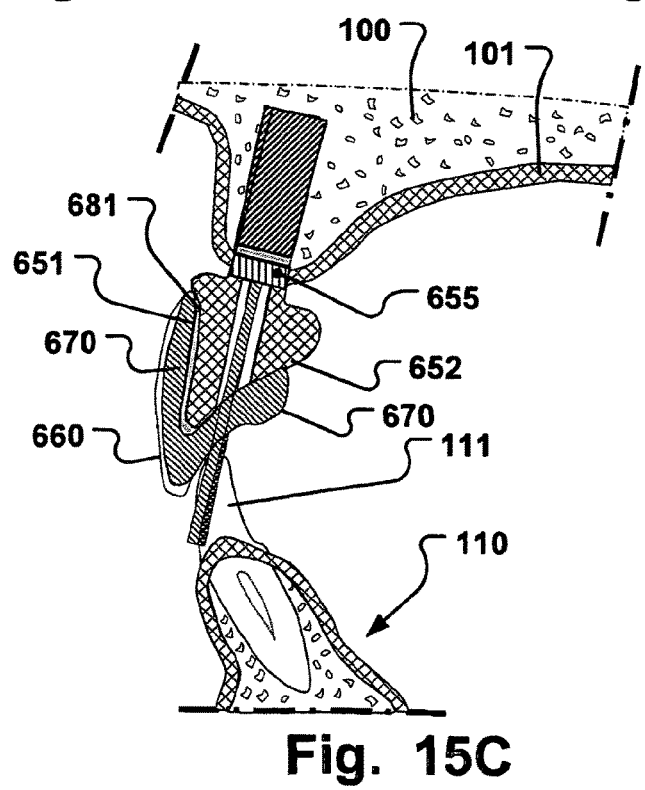
Fig. 15C

SYSTEM AND METHOD FOR PLANNING A FIRST AND SECOND DENTAL RESTORATION

CROSS-REFERENCE TO RELATED APPLICATIONS

This application is a national stage application under 35 U.S.C. § 371 of PCT Application No. PCT/EP2010/006928, filed on Nov. 15, 2010, which published in English as WO 2011/057809 on May 19, 2011, and which claims priority benefit of European Patent Application No. 09014293.6, filed on Nov. 16, 2009, the entire contents of which applications and publication are herein incorporated by reference in their entirety.

BACKGROUND

Field

This invention pertains in general to the field of digital dental design. More particularly the application relates to computer based virtual planning of dental restorations, e.g., comprising dental restoration, as well as for methods of providing components for the dental restoration including the dental restoration, or components related to the dental restoration to be used during a dental restorative procedure, based on production data which is based on the virtual planning.

Description of Related Art

Computer based virtual planning of dental restorations is well established within the field of digital dental design. However, there is still a need in some cases for improving known methods and systems.

For instance, in U.S. Pat. No. 6,814,575 ('575) a computer based dental design method is disclosed. However, the disclosed method still requires time consuming manual work. In '575 a denture is scanned that previously is prepared manually and has a fixed, manually determined teeth setup. Placement of dental implants is virtually planned, based on scan data of the patient's gum, jawbone and tissue structure, and of the manually prepared denture placed over the gum. The implants are positioned in jaw bone tissue based on a locked position of the scanned denture. Hence, the method disclosed in '575 is limited by fixed positions of the manually prepared denture. In FIG. 5 of '575 at position 39, false teeth of the reference denture are scanned. Based on this data, the implants' positions are chosen in a virtual planning. In FIG. 15 of '575 it is illustrated that an implant is adjusted, and the scanned and manually prepared denture (43, 44) is fixed. This computer based method thus lacks flexibility. Moreover, no data is provided to the technician manually preparing the denture, which is related to an appearance or position of facial tissue when the denture is placed over the gum. Thus, the final dental restoration, partly based on the denture, may not be optimal for the patient in terms of fit or aesthetics.

Hence, an improved method or system for virtually planning a dental restoration and/or for providing production data for a component related to the dental restoration based on the virtual planning can be advantageous and in particular allowing for increased flexibility, cost-effectiveness, versatility, patient comfort, patient satisfaction with the restoration and/or outcome of a medical installation procedure and/or optimal calculation of dental restoration shape and/or positions can be advantageous.

SUMMARY

Accordingly, certain embodiments seek to mitigate, alleviate or eliminate one or more deficiencies, disadvantages or issues in the art, such as the above-identified ones, singly or in any combination by providing a method, a system and a computer program according to the appended patent claims.

A dental restoration may thus be virtually planned, and produced from data based on that planning, which restoration can be optimal for the patient in terms of fit, and/or aesthetics.

More precisely, a first dental restoration can be virtually planned. Then the dental restoration can be at least partly produced, and/or at least one product related to a medical procedure for installing at least a portion of said first dental restoration in an oral cavity of a patient can be produced. The dental restoration can be at least partly arranged in the oral cavity and a factual situation is registered based on the first dental restoration when at least partly installed in the oral cavity of the patient. Scan data can be provided for the factual situation and virtual planning can be re-entered for planning a second dental restoration for the patient, wherein the first dental restoration can be adjusted to the factual situation in dependence of the scan data.

According to a first aspect, a method of planning a dental restoration is provided. The method may at least be partially computer based. The method may comprise virtually planning a first dental restoration for the patient; providing first production data based on the planned first dental restoration useful for production of the first dental restoration and/or at least one product related to a medical procedure for installing at least a portion of the first dental restoration in an oral cavity of the patient; providing scan data comprising factual position data and/or factual shape data based on at least a portion of the first dental restoration after modification thereof; virtually planning a second dental restoration for the patient, comprising adjusting the planned first dental restoration in dependence of the scan data, and providing second production data based on the planned second dental restoration useful for production of the second dental restoration.

According to a second aspect, a method of production of a dental restoration having a desired fit or a product related to a medical procedure for installing the dental restoration in a patient is provided. The method may comprise receiving production data from the computer-based method of the first aspect, and can further comprise a) producing the first dental restoration or the product related to a medical procedure for installing at least a portion of the first dental restoration based on the first production data; and/or b) producing the second dental restoration based on the second production data.

According to a third aspect, a computer-based system for virtually planning a dental restoration in a patient is provided. The system may comprise a processing unit adapted to virtually plan a first dental restoration for the patient; provide first production data based on the planned first dental restoration useful for production of the first dental restoration and/or at least one product related to a medical procedure for installing at least a portion of the first dental restoration in an oral cavity of the patient; provide scan data comprising factual position data and/or factual shape data based on the first dental restoration when at least partly installed in the oral cavity of the patient; virtually plan a second dental restoration for the patient, comprising adjusting the planned first dental restoration in dependence of the scan data, and provide second production data based on the planned second dental restoration useful for production of the second dental restoration.

According to a further aspect, a method can provide production data for a component related to the dental restoration. The method may comprise the method of the first aspect recited above and providing the dental restoration data as production data based on the virtual planning for producing at least a portion of the first and/or second dental restoration or components related thereto.

According to yet another aspect, a computer program for virtually planning a dental restoration in a patient, for processing by a computer is provided. The computer program can comprise code segments for virtually planning a first dental restoration for the patient; providing first production data based on the planned first dental restoration useful for production of the first dental restoration and/or at least one product related to a medical procedure for installing at least a portion of the first dental restoration in an oral cavity of the patient; providing scan data comprising factual position data and/or factual shape data based on the first dental restoration when at least partly installed in the oral cavity of the patient; virtually planning a second dental restoration for the patient, comprising adjusting the planned first dental restoration in dependence of the scan data, and providing second production data based on the planned second dental restoration useful for production of the second dental restoration.

According to yet another aspect, a first dental restoration is provided. The first dental restoration may be a try-in restoration for controlling a desired fit of a desired dental restoration in an oral cavity of a patient, wherein the try-in restoration can be modifiable to provide the desired fit, and can comprise at least one recess for an impression material for receiving a coronal portion of a dental implant for providing scan data of a factual position and orientation of the at least one dental implant, wherein the scan data can be useable in virtually planning a second dental restoration having the desired fit.

In some embodiments, the computer program can be embodied on a computer-readable medium, and/or enables carrying out of a method according to the first aspect, and/or is implemented in a system of the above aspect.

The aforementioned modification may comprise modification by medical implants of the first dental restoration that are implanted and may have a position that may be different from the planned position. The factual position is registered, e.g., by means of the implant's connection interface that can be registered and for which data can be provided as factual position data in the modified first dental restoration.

Modification of the first dental restoration may comprise change, adapt, adjust, reshape, redo, revise, or alter of at least a portion thereof.

Further embodiments are defined in the dependent claims, wherein features for the second and subsequent aspects are as for the first aspect mutatis mutandis.

Some embodiments provide for consistent, predetermined results of dental design. Guesswork, as previously based on manual adjustments by several persons involved in the design and production process of dental restoration, can be eliminated.

Some embodiments can provide for facilitated virtual planning of dental restorations, in particular in edentulous patients with improved precision.

Some embodiments can provide for a more effective design of dental restorations, and some embodiments can provide for increased flexibility of the dental design, as compared to the state of the art. The digital data thus available and provided for enabling a virtual environment can provide for versatility in an improved dental design, based on virtual planning of a dental restoration including components such as a dental restoration, e.g., having a bridge framework, and one or more dental implants.

Some embodiments can provide for improved precision of dental design, e.g., thanks to the minimized number of manual steps for planning and production of a dental restoration. Previously necessary manual steps, e.g., related to the use of a gypsum model, can be eliminated.

Some embodiments can provide for an optimized calculation of dental implants' positions in jaw bone tissue, e.g., with regard to patient fit, and/or aesthetics for instance related to important issues for the patient, such as a pleasant smile appearance when the dental restoration is installed in the patient.

Some embodiments can provide for iterative adjustment and verification of a dental design. This was not possible hitherto, e.g., as erroneous excessive carving from a wax-up appliance meant that the appliance had to be discarded and a new appliance had to be manually created in a time consuming manner.

Some embodiments can provide for improved time efficiency. Digital data may be sent from a dentist location to a dental technician location. The latter location may be remote. The dental technician may then produce a physical model for verification by the dentist. Alternatively, production of a dental model can be feasible at the location of the dentist. This procedure can be more time effective than the manual procedures of the state of the art.

Some embodiments can provide for more effective creation of aesthetically pleasing dental restorations. The patient may be provided with a dental restoration that supports facial tissue in a desired manner, e.g., to provide a pleasant smile.

Some embodiments can provide for a pre-visualization of dental restorations including soft tissue and facial tissue, which can be particularly advantageous for cosmetic cases.

Some embodiments can provide for increased patient case acceptance, e.g., thanks to reduced patient time at the dentist, exact fitting of restorations, reduced costs, satisfactory results of dental restorations with regard to aesthetic considerations, flexibility of planning of desired results, etc.

Some embodiments can provide for an increased number of various products or components that may be produced from production data based on virtual planning of a dental design. The products can include temporaries, dental bridge frameworks, surgical templates for drill guided dental surgery, etc. As intermediate steps, such as manual production of dental models, or digitization of such models, may be reduced, the number of sources for errors can also be reduced, and precision of these dental restoration and products or components can be improved.

Some embodiments can provide for production data for making temporaries.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments are capable of will be apparent and elucidated from the following description of embodiments, reference being made to the accompanying drawings, in which

FIGS. 4A and 4B are diagrams of views similar to FIG. 3, illustrating example automatic placement of a teeth setup based on a dynamic library jaw, and manual adjustment thereof;

FIGS. 7A and 7B are diagrams of views similar to FIG. 3, illustrating an example bridge framework planning including a veneering and soft tissue portion;

FIG. 8A is a diagram of a view similar to FIG. 3, illustrating an example temporary restoration or try-in prosthesis creation;

FIGS. 10A and 10B are diagrams of cross sectional views of portions of a real maxilla and mandibula, illustrating an example of adjustment of a try-in prosthesis;

FIGS. 11A, 11B, and 11C are diagrams of cross sectional views of portions of a real maxilla and mandibula, illustrating an example of registration of a factual implant position and occlusion;

FIGS. 12A and 12B are diagrams of cross sectional views of portions of a real maxilla and mandibula, illustrating an example of a healing phase with a soft tissue supported temporary restoration, and a screw retained restoration;

FIGS. 13A, 13B, 13C, 13D, and 13E are diagrams of cross sectional views illustrating examples of alternative, implant replica based, model castings from an impression tray or a try-in prosthesis;

FIGS. 15A, 15B, and 15C are diagrams of cross sectional views illustrating an example of updating of a bridge framework planning.

DETAILED DESCRIPTION OF CERTAIN EMBODIMENTS

Figure 1:
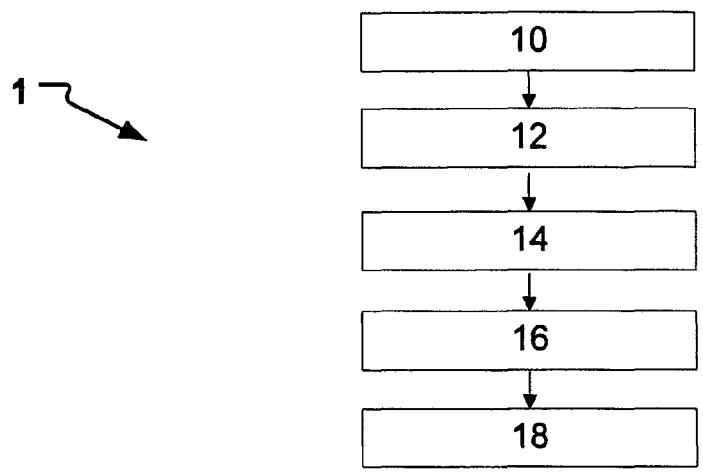
FIG. 1 is a flowchart of an example method of virtually planning a dental restoration and of producing elements for the dental restoration.

Specific embodiments will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope to those skilled in the art. The terminology used in the detailed description of the embodiments illustrated in the accompanying drawings is not intended to be limiting. In the drawings, like numbers refer to like elements.

FIG. 1 is a flowchart of a method 1 of virtually planning a dental restoration. The method 1 may also comprise planning of a dental restorative procedure including installation of at least a portion of the dental restoration planned using the method. The dental restoration may be installed in a real dental restorative procedure corresponding to the previously virtually planned procedure. During the procedure, a dentist may, for instance, use a surgical template produced from production data provided by the method of virtually planning the procedure for implanting one or more dental implants in jaw bone of the patient.

In more detail, the embodied method 1 can be an at least partly computer-based method of virtually planning a dental restoration in a patient.

The method 1 can comprise virtually planning 10 a first dental restoration for the patient, and providing 12 first production data based on the planned first dental restoration useful for production of the first dental restoration and/or at least one product related to a medical procedure for installing at least a portion of the first dental restoration in an oral cavity of the patient.

The method 1 can further comprise providing scan data 14 comprising factual position data and/or factual shape data based on at least a portion of the first dental restoration after modification thereof. The first dental restoration can be modified to a factual patient situation. The scan data may be generated when the first dental restoration, or a portion thereof, is installed in the oral cavity of the patient. The scan data may alternatively, or in addition, be generated when the dental restoration is attached to a model of the patient.

Then the method 1 may continue with virtually planning 16 a second dental restoration for the patient, which can comprise adjusting the planned first dental restoration in dependence of the scan data, and providing second production data 18 based on the planned second dental restoration useful for production of the second dental restoration. Scan data of the factual first dental restoration situation of the oral cavity is re-entered into planning. The factual first dental restoration situation can comprise, for instance, a position and orientation of a dental implant, such as a connection interface thereof, that can be implanted in the patient based on the planning. The factual first dental restoration situation may also comprise shape data of the first dental restoration. The shape data may be provided of a real first dental restoration that can be modified in relation to the planned first dental restoration. The shape data may, for instance, be of a try-in prosthesis that is adapted to patient specific needs or desires, e.g., anatomical restrictions or aesthetic wishes.

The scan data may be generated in various manners, e.g., surface scanned or volumetric scanned, such as impression based, or based on a model thereof, optionally including at least one dental implant position. Scan data comprises data of a modified first dental restoration for a second dental restoration.

The scan data can be re-entered into virtual planning, and the virtually planned first dental restoration can be adjusted based on the scan data in order to virtually plan a second dental restoration.

The virtual planning 10 of the first dental restoration is now described in more detail with reference to FIGS. 3 to 9A. The step of providing scan data 14 is elucidated in more detail below with reference to FIGS. 9B-14, and the step of virtually planning 16 the second dental restoration for the patient is illustrated with reference to FIG. 15.

The virtual planning 10 of the first dental restoration is now described in more detail with reference to FIGS. 3 to 9A. The first dental restoration can be, for instance, a try-in prosthesis (e.g., shown in FIGS. 8A, 8B), or can comprise at least one dental implant (e.g., shown in FIGS. 9B,C). The product related to the procedure for installing at least a portion of the first dental restoration in an oral cavity of the patient can be, for instance, a surgical template (shown in FIGS. 9A, B). A first portion of the dental restoration can be, for instance, a dental implant, and a second portion of the dental restoration can be, for instance, a dental prosthesis or a framework thereof.

Various methods may be applied to virtually plan the first dental restoration. Below a method is described using data from an envelope guide, which is in particular advantageous as facial tissue topology can be considered in the planning of a dental restoration. However, other methods of virtual planning may be used, which lead to a planned first dental restoration.

Figure 3:
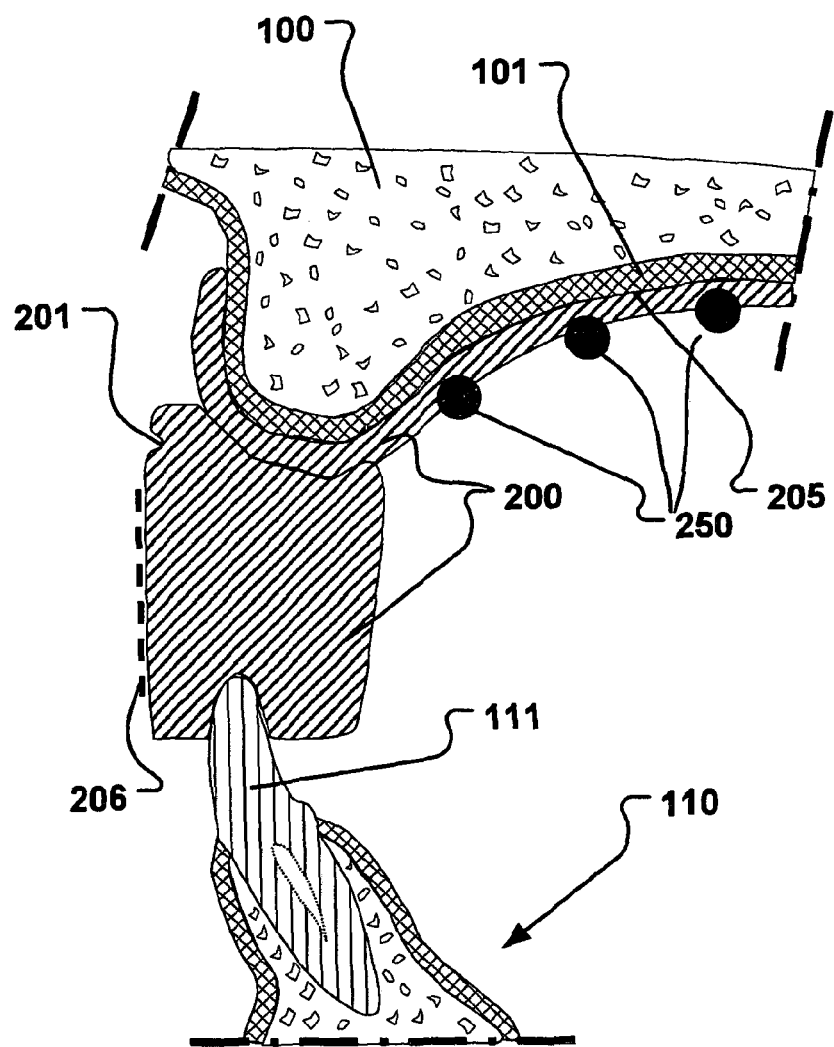
FIG. 3 is a diagram of a cross sectional view of example portions of a maxilla and mandibula in a virtual environment for planning a dental restoration based on imported scan data, including an envelope guide in a form of a wax plate for providing soft tissue boundary information.

Now turning to FIG. 3, a cross sectional view of portions of a maxilla and mandibula can be shown in a virtual environment for planning a dental restoration based on imported scan data, including an envelope guide in the form of a wax plate for providing soft tissue boundary information.

An envelope guide and related products and procedures are described in detail in the European patent application EP09014296.9 with the title "SYSTEM AND METHOD FOR PLANNING AND/OR PRODUCING A DENTAL PROSTHESIS" concurrently filed with the present application on Nov. 15, 2010 by the same applicant, which hereby is incorporated by reference in its entirety for all purposes.

In FIG. 3, portions of a maxilla 100 and a mandibula 110 can be illustrated in a virtual environment based on imported anatomical scan data. The anatomical scan data can provide information for an anatomical situation of a patient. The anatomical scan data may, for instance, be provided from X-ray, volume scanning, such as Magnetic Resonance (MR), Computed Tomography (CT), and/or surface scanned impressions or dental models of the oral anatomy. The anatomical scan data can provide information for jaw bone tissue and/or soft tissue of an oral cavity of the patient. For instance, impression tray based scanning provides first anatomical scan data for an outer surface of gingival soft tissue, and/or remaining teeth, and e.g., CT-scanning, provides second anatomical scan data for the jaw bone tissue. The combined first and second anatomical scan data may be merged into a single set of anatomical scan data representing the anatomical situation of the patient. The combined data may be merged into a single scan data representing the anatomical situation, which is, for instance, described in European patent application EP09006665.5 or WO2008/083857 of the same applicant as the present application, which are incorporated herein by reference in their entirety for all purposes.

In certain embodiments, anatomical data may only comprise information of the anatomical situation in the oral cavity and related bone tissue as such. Boundary information or data elements related to facial tissue, like lip tissue or cheek tissue, can be provided based on an envelope guide 200.

In the illustrative example of FIG. 3 an edentulous maxilla 100 is illustrated, while the mandibula 110 has remaining teeth, as illustrated by tooth 111. In FIG. 3 a representation of the envelope guide 200 is shown for providing boundary information. Input data for the envelope guide 200 can be suitably generated from a real envelope guide, e.g., by surface scanning the real envelope guide. The envelope guide 200 can be adjusted to the specific patient anatomy of the oral cavity. The envelope guide can be made of a material which allows adaptation of its external shape to the patient specific conditions, e.g., by removing material therefrom, and/or reshaping the material, or and/or adding material, usually by a dentist in a dialogue with the patient in order to achieve a desired result with regard to facial tissue in relation to a dental restoration. In this manner, for instance, a desired lip support surface 206 can be created, as illustrated by the dashed line in FIG. 3.

The envelope guide can be put entirely in the patient's mouth for transferring information also in relation to facial tissue. The envelope guide can be put in abutment with an anatomical structure of the oral cavity. Further, the envelope guide can have a surface that is substantially complimentary in shape to the specific shape of the oral cavity. A portion of an envelope guide conforms for instance to the ridge of the upper and/or lower jaw, such as illustrated in the example of FIG. 3, where an upper portion 205 of the envelope guide 200 has a shape substantially complementary to the shape of the outer surface of maxillary soft tissue 101 as well as to the bite portion of the mandibular tooth 111.

The envelope guide 200, when scanned, can provide for envelope data thereof. The envelope data may comprise data of an envelope portion of the envelope guide. The envelope portion may correspond to a support surface for facial tissue, which can provide for the facial tissue to be oriented in a desired result when the dental restoration is installed in the oral cavity of the patient. The support surface for the facial tissue may comprise the lip support surface 206, as illustrated by the dashed line in FIG. 3.

Remaining portions of the envelope guide can provide for envelope data of the remaining portions thereof. For instance, as illustrated in the example, a portion of the envelope data can provide information for the shape of the outer surface of the maxillary soft tissue. Other portions may provide data related to an occlusion portion of the envelope guide 200 that can be positioned adjacent and along the dental arch, as illustrated in FIG. 3 adjacent to the tooth 111. In this manner the envelope data of the envelope guide can have a fixed spatial relation for matching with the anatomical scan data, e.g., based on a common occlusion portion of the envelope guide and the oral cavity, or on a common outer surface of the maxillary soft tissue.

The envelope guide can be converted to digital envelope data, which can be merged with the anatomical scan data to provide a model such as shown in FIGS. 3, 4A, and 4B for computer-based virtual planning of a dental restoration in the oral cavity.

The anatomical scan data, e.g., provided from an impression tray with fiducial markers, as described above, can comprise data for surfaces of the oral cavity. By scanning the impression tray both in the oral cavity and separately by surface scanning, and using the fiducial markers scanned in both scannings, the position of the surface of the oral cavity relative jaw bone tissue can be known. In turn, the envelope data of the envelope guide can have a fixed spatial relation to the anatomical scan data based on interfacing complementary surfaces of the envelope guide and the oral cavity. The complementary surfaces can be conforming, e.g., a bite portion of remaining teeth and the corresponding complementary surface in the envelope guide, or gum surfaces and corresponding complementary surface in the envelope guide. By surfacing scanning the envelope guide, the envelope data can comprise data for the complementary surfaces for which data can be comprised in the anatomical scan data, allowing for a matching and subsequent merging of the envelope data and anatomical scan data.

In addition, or alternatively, the envelope guide may comprise fiducial markers, as illustrated in the example of FIG. 3 by the three spherical elements 250 arranged at the surface oriented towards the inside of the oral cavity at the portion of the envelope guide arranged at the soft tissue of the maxilla. By scanning the patient wearing such an envelope guide, e.g., with a cone beam CT scanner, the relation between the complementary surfaces may be determined in a similar manner as described above without the need of an impression tray.

The envelope data may be merged with the anatomical scan data based on known surface matching techniques for finding the complementary surfaces which can be conforming. The envelope data may be surface matched based on the bite portion, or gum surfaces and corresponding complementary surface in the envelope guide.

The envelope guide 200 can comprise one or more markings 201 carved by the dentist during adaptation to the patient.

The markings can comprise, for instance, a first marking 201 for a desired smile line, which can define a line of how large a portion of the teeth is visible when the patient smiles. Further, the smile line may provide if, and how large a portion of the interdental papilla is visible when the patient smiles. The first marking 201 thus can provide a measure for positioning and sizing virtual teeth correctly in relation to this desired result.

The markings may further comprise a second marking (not shown) for a central incisiory position, e.g., an incisal line position between central incisor teeth, also called a dental midline. The markings may further comprise a third and fourth marking (not shown) for desired positions of left and right canines in the envelope guide.

The markings can be made based on experience of the dentist. The smile line may be marked in a dialogue with the patient, e.g., a low, average, or high smile line. The desired position of the smile line is marked in the envelope guide and provides a basis for the choice of library teeth with regard to a length thereof. The central incisiory position and desired position of canines can provide information to position teeth from a teeth library at a correct position along the dental arch. These markings can be taken advantage of in the virtual planning described below, as will be explained below.

Thus, the envelope guide can provide boundary information elements, amongst others, for a spatial orientation of a lip support in rest, an extension of a smile line that is desired to be positioned in relation to the teeth, as well as information for an inclination and/or length of teeth, the position of a cementoenamel junction of such teeth, as well as a position of certain teeth along the dental arch. The cementoenamel junction can be a location of a tooth where the enamel meets the cementum, which covers the root of a tooth. In a dental restoration this can be the junction of the prosthetic tooth enamel to the prosthetic gingiva. Further, the position of interdental papilla may be provided by the boundary information elements based on the envelope guide.

The envelope data of the envelope portion of the envelope guide 200 thus can correspond to a support surface of a desired dental restoration for facial tissue, which can provide for the facial tissue to be oriented in a desired result when the dental restoration is installed in the oral cavity of the patient. The simulated outer envelope can provide a basis for virtually planning a desired dental restoration in the oral cavity based on the envelope data. The desired dental restoration may be adjusted relative to the outer envelope.

The first dental restoration may comprise at least one of a virtual tooth or a simulated soft tissue surface. The simulated soft tissue surface can be, for instance, a simulated external buccal gum surface 220, lingual gum surface 221, or an internal palatal gum surface 225 or an external palatal gum surface 226 of the desired dental restoration; see FIG. 4A. Modification of these soft tissue surfaces during virtual planning is described below, e.g., with reference to FIG. 5.

FIGS. 4A and 4B are views similar to FIG. 3, illustrating an example of automatic placement of a teeth setup based on a dynamic library jaw, and manual adjustment thereof.

The virtually planning 10 a first dental restoration for the patient of the method 1 may comprise providing at least one virtual tooth 302. The method may thus comprise virtually planning the first dental restoration based on a teeth-setup using a teeth library. The method may comprise adjusting a position of at least one library tooth from the teeth library for the teeth-setup, such that the library tooth is located relative to an outer boundary defined by the envelope guide. The outer contour of the envelope guide can provide a rough estimate of the desired position of a final dental restoration and can be used as an input in digitized form for guiding a precise planning of the dental restoration. The outer contour of the envelope guide thus can provide a target guide surface in relation to which a buccal orientation of a dental restoration of the dental restoration can be aimed at.

Virtually positioned markers may be used as fix points in space. Teeth from a teeth library can then adjusted in relation to these fix points. The fix points can be, for instance, created by marking points manually in the coordinate system of the graphical environment of the virtual planning system or software. The points can be marked in order to define where certain teeth are to be positioned. This can be made in order to become independent of the manner in which markings may be made in the envelope guide by the dentist. By providing the virtual markings during the virtual planning, mistakes or mix-ups of the position of teeth (tooth design parameters) based on the envelope guide can be avoided. Furthermore, this can provide for a quick way of setting up of the teeth set-up. In a practical example, e.g., the position in space of the coronal end of the left canine can be virtually marked to be at a first position, then the position of the central incisory line can be virtually marked to be at a second position, etc.

The library teeth can be positioned at a suitable position along the crest to form a dental arch in the maxilla 100. Initial positioning may be made manually or automatically.

Automatically positioning may for instance be based on recognition of specific markers that can be comprised in the envelope guide and positioned there by the dentist. For instance, a specific shape of markers may be linked to a specific type of teeth for facilitating this automatic recognition, e.g., a triangular shape for a canine, a square shape for an incisor, etc.

Manual initial positioning may be based on the markers in the envelope guide.

Alternatively, or additionally, the initial position in the dental arch may be based on anatomically fixed landmarks, and/or experience of a dentist performing suitable manipulations in the computer based virtual environment.

Anatomically fixed skull reference points may be used as landmarks for initially positioning one or more library tooth based on the anatomically fixed skull reference points prior to the adjusting of a position of the library tooth/teeth of a teeth setup. A method of positioning library teeth from a teeth library is disclosed in WO2008/145293 of the same applicant as the present application, which is incorporated herein by reference in its entirety for all purposes. The method disclosed in WO2008/145293 may be based on anatomically fixed landmarks for determining the position of certain teeth along a dental arch in an edentulous jaw, and for determining an occlusion line.

As can be seen in FIGS. 4A and 4B, the virtual tooth 302, as well as the remaining teeth of the teeth setup, can be positioned in relation to an outer envelope of the envelope guide 200 in order to provide an advantageous support for facial tissue. The envelope guide 200 can provide an envelope in relation to which the library teeth are to be arranged. The outer envelope can correspond to an internal surface of the facial tissue in a desired rest position against the library tooth 302.

The virtual tooth 302 from the tooth library may be positioned strictly within the outer envelope, as illustrated. In other embodiments, the virtual tooth 302 may be positioned crossing the outer envelope. This may be necessary due to a number of reasons, e.g., anatomical or aesthetical reasons, limited number of library teeth, strength of restoration, possible position of implants, etc. For automatically positioning of a virtual tooth 302 it may be advantageous to position the tooth 302 within the outer envelope. A manual adjustment may be made from this initial position of virtual tooth 302 during subsequent virtual planning.

Positioning of the library teeth may then manually be changed in the virtual environment from that initial position, as illustrated in FIG. 4B, e.g., by taking into consideration a desired position of facial soft tissue for adjusting the initial position of library teeth accordingly. As explained above, the position of the library teeth may be adjusted with regard to inclination and/or a desired length. In addition, or alternatively, the tooth may be suitably chosen from the teeth library to have a desired position of a cementoenamel junction along such tooth. Further, the position of prosthetic interdental papilla may be chosen as desired, based on the aforementioned boundary information elements.

An envelope guide is not necessary for all embodiments.

For instance, the initial position of the virtual tooth 302, may be changed to provide an optimal teeth setup. The position, size and/or shape of a library tooth may, for instance, be changed for creating a desired smile line. In FIG. 4B such a virtual change is illustrated of a tooth position in relation to the outer envelope of envelope guide 200. Changing the position of the library tooth may comprise adjusting an inclination of a longitudinal axis of the library tooth in relation to jaw bone tissue, and adjusting a distance of a coronal end (front end opposite the apical root portion of the tooth) of the library tooth to an outer surface of the jaw bone tissue. The change may be made for creating a desired smile line. Alternatively, or in addition, the change may be made of the spatial position, volumetric size, or length of the virtual tooth such that the virtual tooth can be located relative to the outer envelope.

When changing the initial position of a library tooth, it may comprise verifying the position of the at least one library tooth and re-adjusting the position of the at least one library tooth relative to the outer boundary.

Thus, an anatomically and aesthetically correct teeth-setup for the first dental restoration can be provided in the virtual planning.

Now, a correct rehabilitation position can be determined for the teeth setup and any remaining elements or steps for a dental restoration may be planned from this starting position, such as positioning of dental implants, planning of soft tissue portions of dental restorations, etc.

Facial tissue when in rest against the teeth, when installed in the oral cavity of the patient—based on data from the virtual planning, provides a desired aesthetically correct appearance of facial tissue and/or restoration relative to facial tissue. The final result may be simulated in the computer based virtual environment, and verified prior to producing elements for the second dental restoration.

Verification may, e.g., be made by a try-in prosthesis produced from a first production data output from the virtual planning. The method of planning the dental restoration may comprise planning of teeth and planning implants. Other components like a surgical template or a bridge framework (which may be based on a library) may be provided. The bridge framework can be adapted to the virtual teeth and the soft tissue.

Based on this virtual planning, a dental restoration in a form of a try-in prosthesis may be produced, e.g., by rapid prototyping techniques, in order to check if the virtual planning was done well. All data can be already available in the system and production data for the dental restoration, e.g., the try-in prosthesis, can be readily generated in the computer based environment. The try-in prosthesis can be provided for verification purposes prior to finalizing the virtual planning and producing the final dental restoration.

The try-in prosthesis can be installed in the patient. The dentist may now check if the lip support is as desired, if the smile line is as desired, etc. The patient or dentist may now make changes in the virtual environment based on the information obtained from this verification.

The try-in prosthesis may only be used during this verification, or the try-in prosthesis may be a temporary restoration that can be left in the patient until a final restoration is produced and ready for installation in the patient.

The try-in prosthesis may, for instance, be soft tissue supported, or the try-in prosthesis may be supported by at least one dental implant in the patient. In the latter case, a surgical template and the try-in prosthesis may be produced. The dental implants can be installed in the patient using the surgical template. Then the try-in prosthesis can be affixed to the dental implants. The correct fit of the dental restoration, now in a form of the try-in prosthesis, can be checked and verified with the patient. In case the fit is fine, the final dental restoration can be produced and installed. In case the try-in prosthesis reveals that the dental restoration is not satisfactory, the virtual planning can be adjusted based on the information obtained from this verification. As the dental implants are now installed in the patient, the connection interface of the dental implants towards the bridge framework can be given as a factual position in the virtual planning environment. In certain embodiments, the factual position is not changed in the virtual environment, but taken as a basis for continued planning.

It should be noted that when the virtual planning is re-started and the dental restoration may be adjusted, all data may already be present in the computer based system. There may be no need for acquiring further data. However, continued virtual planning may need to only be made of those parts of the dental restoration that may not be related to a registered factual position or shape. Portions that correspond to a factual position and/or shape that has been modified from planning of the first dental restoration can be adapted to this factual position and/or shape when virtually planning the second dental restoration. The registered factual position and/or shape portions can define a new initial position with reference to the first planned dental prosthesis. The factual position and/or shape can be fixed in the patient and the second dental restoration can be adapted to this factual situation.

In case the dental implants are not implanted at the desired position for some practical reason, data for the actual position of the connection interface of the dental implants may be acquired. This may be done with an impression taken of the connection interface with an impression tray, scanning the impression tray, and matching against soft tissue in the computer environment to enter the data for the actual position and orientation of the implants. Now the dentist may adjust the virtual planning if desired. For instance the bridge framework may be adjusted, or the teeth may be adjusted.

Figure 5:
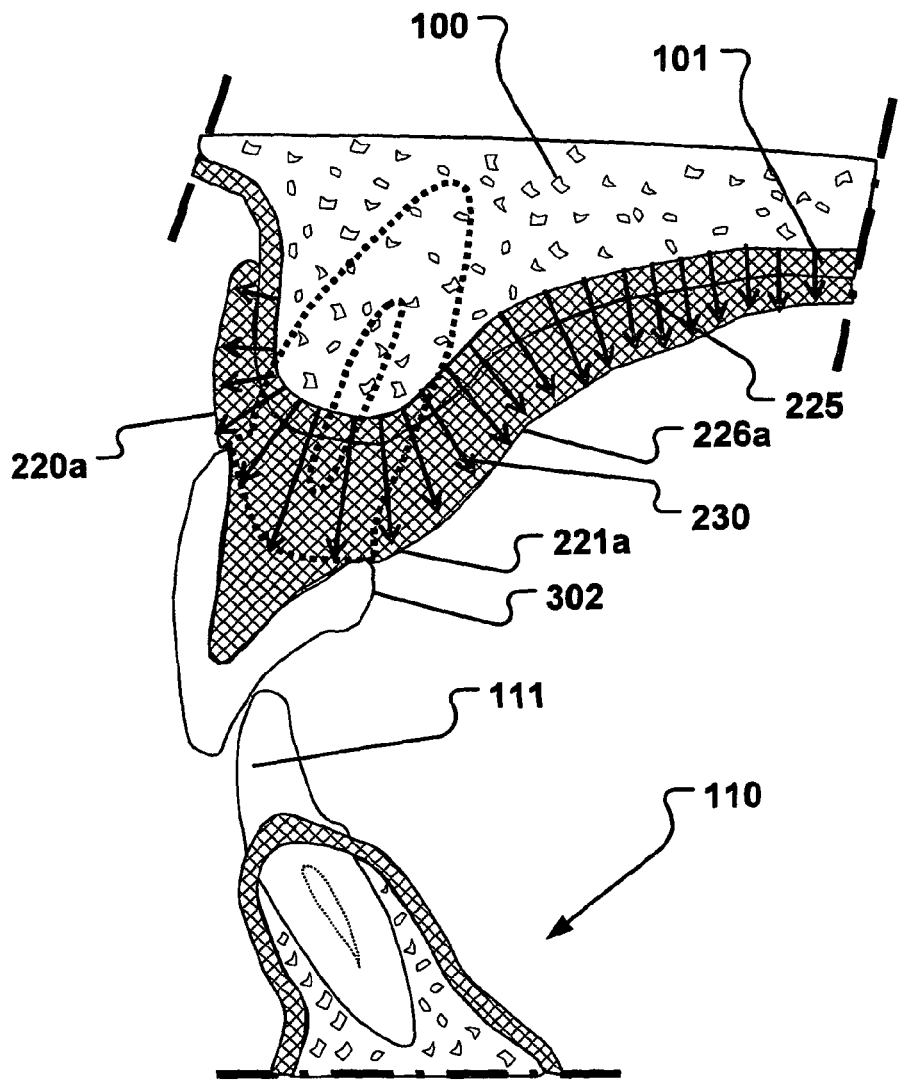
FIG. 5 is a diagram of a cross sectional view similar to FIG. 3, illustrating an example teeth and soft tissue arrangement where soft tissue is chosen from a jaw library and adapted to a patient.

Turning to FIG. 5, modification of soft tissue surfaces during virtual planning is described. The simulated soft tissue surface can be, for instance, a simulated modified external buccal gum surface 220a, a modified lingual gum surface 221a, or a modified external palatal gum surface 226a of the desired dental restoration. An internal palatal gum surface 225 substantially can correspond to or can be based on the digitized soft tissue surface of the patient. An outer surface of the dental restoration thus can correspond to natural form of soft tissue before resorption. A natural form of the jaw crest can be restored to the topography of natural jaw bone tissue. As soft tissue can be substantially not resorbed and changed, this gives a natural position of the soft tissue that can be re-created with the outer surface of the dental restoration.

As illustrated by arrows 230, the modified soft tissue surfaces, such as surface 226a, can be chosen to compensate for bone resorption of the edentulous maxilla. Thus a natural topography of a soft tissue surface in the oral cavity may be restored by a prosthesis based on the virtual planning. The soft tissue may be restored in relation to the bone surface of the jaw bone, as shown in FIG. 5. In FIG. 5 the arrows 230 illustrating this modification of the soft tissue surfaces can have a different length at different portions of the jaw bone. This is due to the fact that bone tissue at the crest can have resorbed to a larger degree than, e.g., palatal jaw bone tissue. The outer surface may then be provided as a portion for the first dental prosthesis.

An example is the soft tissue portion of a try-in prosthesis, temporary prosthesis, or a final soft-tissue supported prosthesis 800 such as shown in FIG. 8A. Here, a digitized soft-tissue surface, based on a surface scanned impression, model or intra-oral scanning can be combined with a Computer-Aided Design (CAD) object based on the first dental prosthesis.

Two surfaces can be combined, wherein one surface can be patient specific, for making a dental restoration.

Figure 8B:
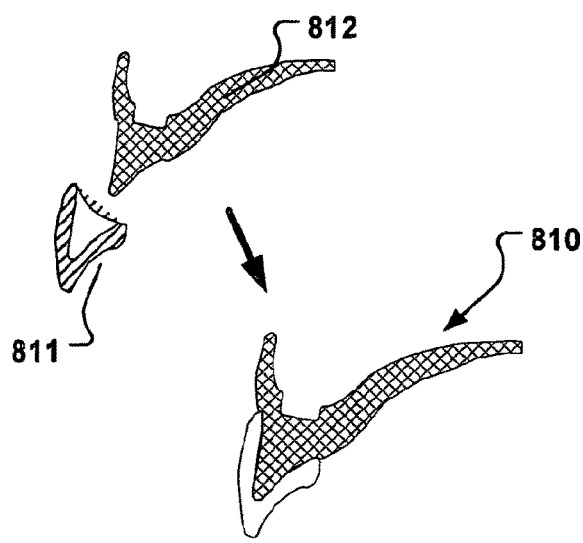
FIG. 8B is a schematic illustration of an example temporary restoration.

The soft tissue data for the corresponding surface of the CAD object may be provided from a soft tissue library. Alternatively, or in addition, the soft tissue data may be scaled, based on anatomical patient data, such as by morphing, or manual adjustment, such as illustrated by arrows 230 in FIG. 5 and described above. The library may comprise one or more objects. The object can be scalable. The objects can comprise soft tissue that is scalable. The try-in prosthesis may then be produced and then modified or adapted to the patient. Planning may then be updated based on re-scanning of the try-in prosthesis for providing a final prosthesis. A cross section through such a try-in prosthesis is shown in FIGS. 8A and 8B. The try-in prosthesis, temporary prosthesis, or a final soft-tissue supported prosthesis 800 may be integrally made in a single monolithic unit (FIG. 8A). Alternatively, the try-in prosthesis, temporary prosthesis, or a final soft-tissue supported prosthesis 800 may be produced as an assembly of several elements, such as illustrated in FIG. 8B.

Soft tissue may, for instance, be chosen from a jaw library and adapted to a patient. As illustrated by arrows 230, the modified soft tissue surfaces 220a, 221a, and 226a of FIG. 5 can be chosen to compensate for bone resorption of the edentulous maxilla. Thus, a natural topography of a soft tissue surface in the oral cavity may be restored by a prosthesis based on the virtual planning. The soft tissue can be restored in relation to the bone surface of the jaw bone, such as shown in FIG. 5. This takes into consideration that soft tissue 101 has a varying thickness, and an advantageous soft tissue reconstruction can be provided in relation to the topography of the jaw bone. However, the natural topography of the soft tissue surface may alternatively, or in addition, be restored in relation to the surface of the soft tissue 101.

In some embodiments, the method of virtually planning a dental restoration can comprise thus adjusting a soft tissue surface of the dental restoration in the oral cavity based on anatomical scan data.

The first dental restoration can be, e.g., a try-in prosthesis, and the adjusting of the soft tissue surface can comprise adapting the try-in prosthesis to an anatomical situation of the patient. For instance, in certain areas of the soft tissue a pressure relief may be desired. In addition or alternatively, the occlusion may be adapted to the occluding teeth.

In some embodiments, the adjusting of the soft tissue surface can be made prior to virtually positioning at least one dental implant for retaining the prosthesis comprising the soft tissue surface in the oral cavity.

In some embodiments, the virtually planning can comprise virtually planning a position of at least one dental implant of the dental restoration. In some embodiments, the virtually planning comprises virtually planning a shape of the first dental restoration, and planning a position of at least one dental implant.

FIGS. 6A, 6B, 6C, and 6D are views similar to FIG. 3, illustrating an example dental implant planning once the virtual tooth is positioned. As illustrated in FIGS. 6A, 6B, 6C and 6D, positions of dental implants 450, as illustrated by the longitudinal axis 600, can be adjusted to the position of the teeth in the teeth setup. The position of the teeth setup can be locked and subsequently, at least one dental implant for anchoring a dental restoration based on the teeth setup can be virtually positioned. This may be performed automatically, manually or semi-automatically. This may, for instance, be made in accordance with the disclosure of WO2008/145293 mentioned above.

Figure 6A:
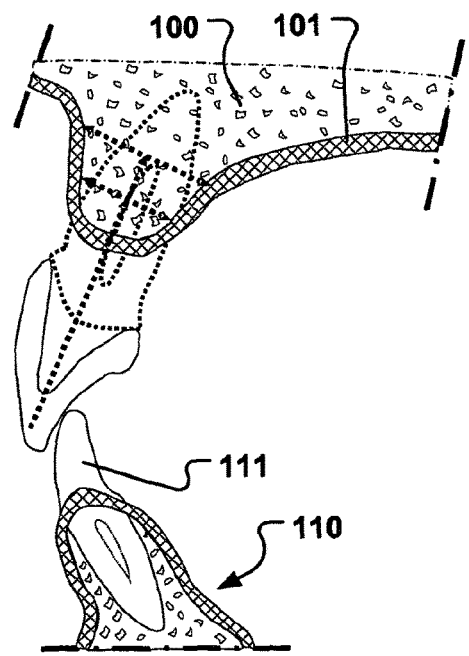
FIGS. 6A, 6B, 6C, 6D are diagrams of views similar to FIG. 3, illustrating example dental implant planning.
Figure 6B:
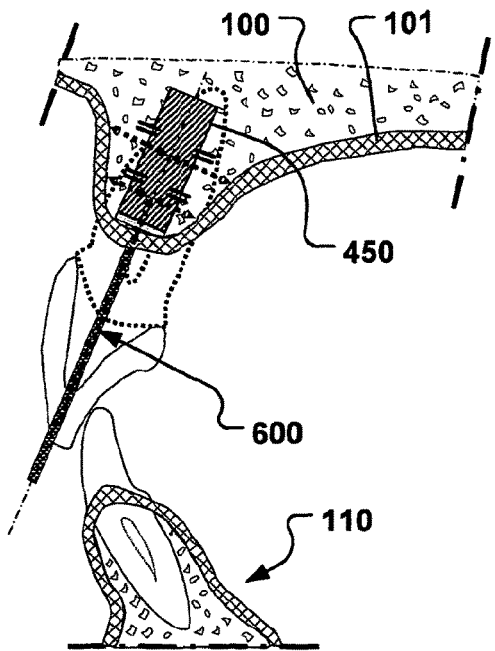

In FIG. 6A it is illustrated how an implant positioning can be calculated based on bone anatomy analysis. The positioning of the dental implant can comprise calculating an implant position in relation to jaw bone tissue and a locked coronal tooth portion, e.g., the position of the virtual tooth may not be modified for planning the position of the implant.

The longitudinal axis of the dental implant can be positioned at a midline of the ridge of the maxilla. This can provide for an advantageous retention of the dental implant in the jaw bone tissue and high mechanical strength therein. The calculated position of implant 450 can be illustrated by the longitudinal axis 600 in FIG. 6B.

Figure 6C:
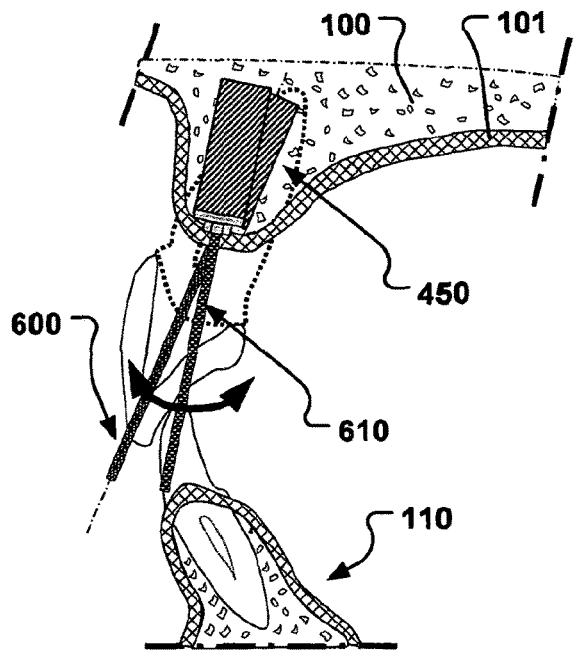

Manual adjustments of the implant position and orientation may be made in the virtual environment to a manually adjusted position. This is illustrated in FIG. 6C, wherein the adjusted position can be illustrated by the longitudinal axis 610.

Figure 6D:
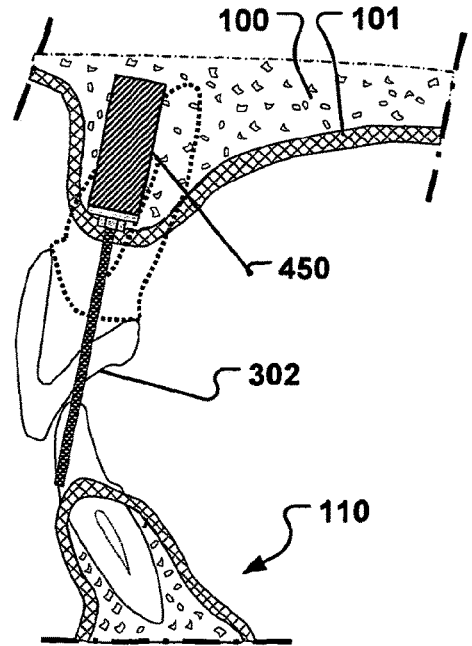

In FIG. 6D an optimized implant positioning is illustrated that can be chosen in dependence on available bone volume and aesthetic criteria. It can be seen that the entry hole in the dental prosthesis can be chosen to be in the buccal area of the tooth 302, where it is hidden and does not interfere with the aesthetics of the dental restoration.

FIGS. 7A and 7B are views similar to FIG. 3, illustrating an example bridge framework planning including a veneering and soft tissue portion.

In FIG. 7A automatic calculation of a bridge framework and production data therefor is illustrated. Production data for a dental bridge framework 650 can be obtained by a cut back technique, e.g., a certain portion of the dental restoration can be removed starting from the outside of the teeth in order to receive the size and shape of the bridge framework. The portion that has been removed is then re-created, e.g., by veneering before the bridge framework is installed in the patient and affixed to dental implants.

The teeth chosen from a tooth library have a pre-defined shape. In order to arrive at the shape of the bridge framework 650 shown in FIG. 7A, a certain portion of the library teeth can be removed, e.g., the library teeth can be cut back in order to arrive at the shape of the bridge framework at the portion carrying the veneering.

Alternatively, or in addition, the bridge framework may be chosen from a library of bridge frameworks. For instance a spline curve (not shown) that follows the teeth set-up may be identified in the computer environment. A bridge framework having the same or a similar spline form may be chosen from the library of bridge frameworks. Starting from the library bridge framework, the remaining dental restoration can be created.

The connection interface of the bridge framework towards dental implants can be chosen suitably, e.g., a certain type such as a Branemark System® connection interface, and with a position and orientation towards the dental implants.

Now the CAD object may be provided as production data for producing the bridge framework.

A calculated bridge framework 650 with veneering 660 and a soft tissue portion 670 is shown in FIG. 7B as the dental prosthesis portion of the first dental restoration, further comprising the dental implant 450.

FIG. 8A is a view similar to FIG. 3, illustrating an example try-in prosthesis creation. First production data can be provided for a try-in prosthesis that is devised to be affixed in the oral cavity of the patient in relation to at least one dental implant. In other embodiments, the first dental restoration may, for instance, be a soft tissue supported temporary prosthesis or a try-in prosthesis.

The first dental restoration that can be virtually planned can comprise, in this embodiment, the aforementioned dental implant 450 to be installed in the patient, as well as a temporary prosthesis to be placed over the gum and receiving the coronal portion of the dental implant 450 in a recess 802. Further, production data can be provided for a surgical template 700 (FIGS. 9A, 9B) for installing the dental implant 450. The temporary prosthesis can be prepared with the recess 802 sized to receive an impression coping 452 (for a try-in prosthesis 800, FIG. 8A) or a healing cap 454 (for a temporary prosthesis 810 as, e.g., shown in FIG. 12A).

In some embodiments, the first dental restoration comprises a try-in prosthesis 800 for controlling a desired fit of a desired dental restoration in the oral cavity of the patient. The try-in prosthesis 800 can be modifiable to provide the desired fit, and can comprise at least one recess 802 for an impression material for receiving the coronal portion of the dental implant for providing scan data of a factual position and orientation of the at least one dental implant. The scan data can be useable in virtually planning a second dental restoration having the desired fit, as described below. The recess 802 can be adapted to receive a cap mounted to a coronal end of the dental implant 450 when implanted, wherein the recess is larger than the cap for receiving the impression material for registering the position and orientation of the dental implant 450. The first dental restoration can thus be positionable on a jaw of the patient when the dental implant 450 is implanted therein and the cap mounted thereon. The cap may be the aforementioned impression coping 452 or healing cap 454.

FIG. 8B is a schematic illustration of a first dental restoration in a form of a temporary prosthesis 810 that is assembled or pre-manufactured of several parts which can be produced based on production data from the virtual planning. The illustrated assembly can comprise a temporary bridge portion 811 and a prosthesis framework 812. The temporary bridge portion 811 may be produced by milling, e.g., an acrylic or a ceramic workpiece. The prosthesis framework 812 may be produced by free-form techniques, such as 3D printing known by the skilled person in production techniques. However, the prosthesis framework 812 and the temporary bridge portion 811 may be produced by the same production technique.

Production data for manufacturing components related to the dental restoration based on the virtually planned teeth setup can be provided. Based on production data provided from the virtual planning, various elements may be produced, including a try-in prosthesis, a dental bridge framework 650, and a surgical drill template 700. Some of these elements, such as the try-in prosthesis or the surgical drill template 700 may be produced by rapid prototyping or milling techniques. The try-in prosthesis may be fully automatically produced, and can facilitate verification of the dental design. The try-in prosthesis may be proof fitted to a gypsum cast 501 of a jaw of the patient. More preferably, in some embodiments the try-in prosthesis may be proof fitted in the patient to verify a correct position of facial tissue in rest, or a smile line. Moreover, the try-in prosthesis may be used for registering a position and orientation of at least one dental implant.

Figure 9A:
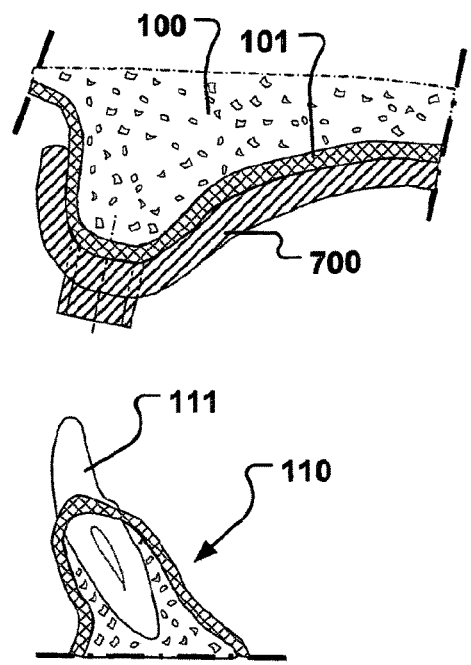
FIG. 9A is a diagram of a view similar to FIG. 3, illustrating an example of a virtually planned surgical template for drill guided dental surgery.

In FIG. 9A an example virtually planned surgical template 700 is shown for drill guided dental surgery. The production data for the surgical template 700 can be determined based on the virtually planned position and orientation of one or more dental implants 450, and the anatomical data of the soft tissue topography of the maxilla 100.

Several embodiments of first dental restorations have been described above, such as a first dental prosthesis; at least one dental implant wherein the first production data can comprise data for a surgical template for installing the at least one dental implant in the patient; a try-in prosthesis; a temporary restoration; or a try-in restoration. Data for producing additional or alternative dental restorations or related products may of course be provided by the virtual planning.

First production data can be provided based on this virtual planning of the first dental restoration. The first production data may be used for producing at least a part of the first dental restoration, elements, and/or components related to the first dental restoration.

Now turning to FIGS. 9B-14, the step of providing scan data 14 (FIG. 1) is elucidated in more detail.

Figure 9B:
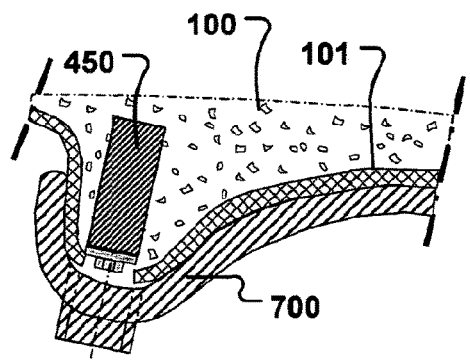
FIGS. 9B, 9C are diagrams of cross sectional views of portions of a real maxilla and mandibula, illustrating an example of surgical template based drill guided dental surgery for implanting a dental implant.
Figure 9C:
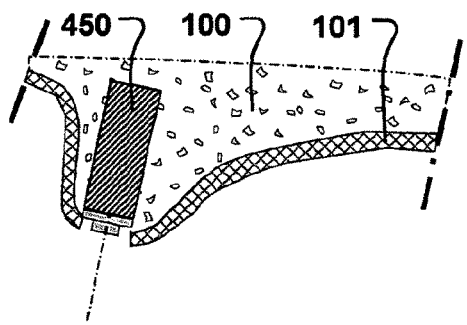

FIGS. 9B and 9C are cross sectional views of example portions of a real maxilla and mandibula, illustrating surgical template based drill guided dental surgery for implanting a dental implant. In FIG. 9B the clinical work, e.g., a medical implantation procedure, for drilling a bore in jaw bone tissue and implanting dental implants is illustrated. A dental implant 450 can be implanted in bone tissue of the maxilla 100, guided by the surgical template 700. The same surgical template may be been previously used for guiding a drill, preparing the bore at the desired position, orientation and depth for the implant. In FIG. 9C the factual anatomical surgery situation can be illustrated, wherein the dental implant 450 has a factual position, which can be registered and factual position data can be generated as described below for continued virtual planning of a second dental restoration. In some embodiments, the second dental restoration can be at least a portion of a complete dental restoration to be supported by the already implanted dental implant(s), e.g., a bridge framework, an abutment, or a single tooth prosthesis.

FIGS. 10A and 10B are cross sectional views of example portions of a real maxilla and mandibula, illustrating an example adjustment of a try-in prosthesis 800. The try in prosthesis 800 can be placed in the mouth in abutment with the soft tissue and a fit in check of occlusion and general aesthetic criteria can be performed in clinical work. A dentist can adjust the teeth by grinding and adding material if required. Grinding is illustrated by a dashed line 350 of the contour of the tooth portion of the try-in prosthesis. Added material 360 is illustrated at the lingual side of the tooth portion, where a dashed line illustrates the original shape of the try-in prosthesis.

FIGS. 11A, 11B, and 11C are cross sectional views of example portions of a real maxilla and mandibula, an example illustrating registration of a factual implant position and occlusion.

FIGS. 11A and 11B illustrate a first variant, where in clinical work an impression can be taken of the implant position by means of the try-in prosthesis 800. Impression material 804 can be filled in the recess 802 of the try-in prosthesis 800. The resulting impression, when the impression material has cured, can correspond to the conforming impression coping 452. Scanning the try-in prosthesis thus can provide scan data for the factual position of the dental implant 450, as well as general aesthetic criteria. In FIG. 11B a bite index 808 is illustrated, which can provide for generating scan data for the factual occlusion.

In FIG. 11C an alternative method of registering factual shape and/or position data is illustrated. An impression can be taken with an impression tray 900. A triple tray may be used for simultaneously registering a topography of the maxilla and mandibula, as well as occlusion data. Scan data may be provided from scanning the cured impression material for factual shape and/or position data. The position of the connection interface of the dental implant can be registered by impression coping 452.

In FIG. 12A a healing phase is illustrated with a soft tissue supported temporary restoration. The surgery situation can be ready for healing with the soft tissue supported temporary prosthesis 810. The healing cap 454 can be received in recess 802. The temporary prosthesis 810 can be made based on first production data provided by the virtual planning method described above.

In FIG. 12B a healing phase is illustrated with a screw retained dental prosthesis 850 on a provisional abutment 380 affixed to the dental implant 450. The screw retained dental prosthesis 850, and optionally a provisional abutment 380, can be made based on first production data provided by the virtual planning method described above.

In FIGS. 13A, 13B, 13C, 13D, and 13E alternative, implant replica based, model castings are illustrated from an impression tray or a try-in prosthesis.

Figure 13A:
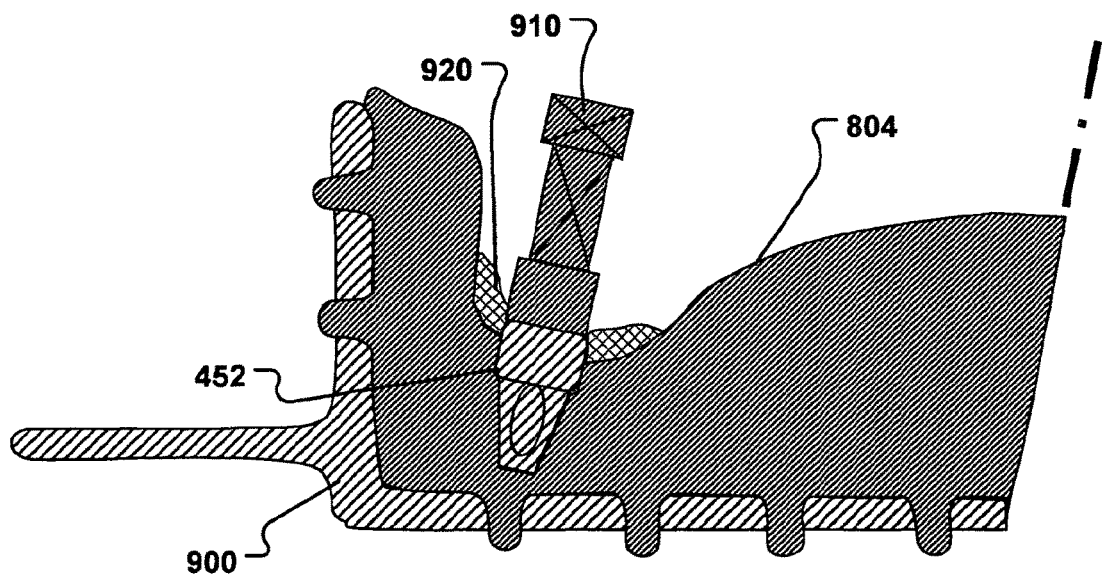
Figure 13B:
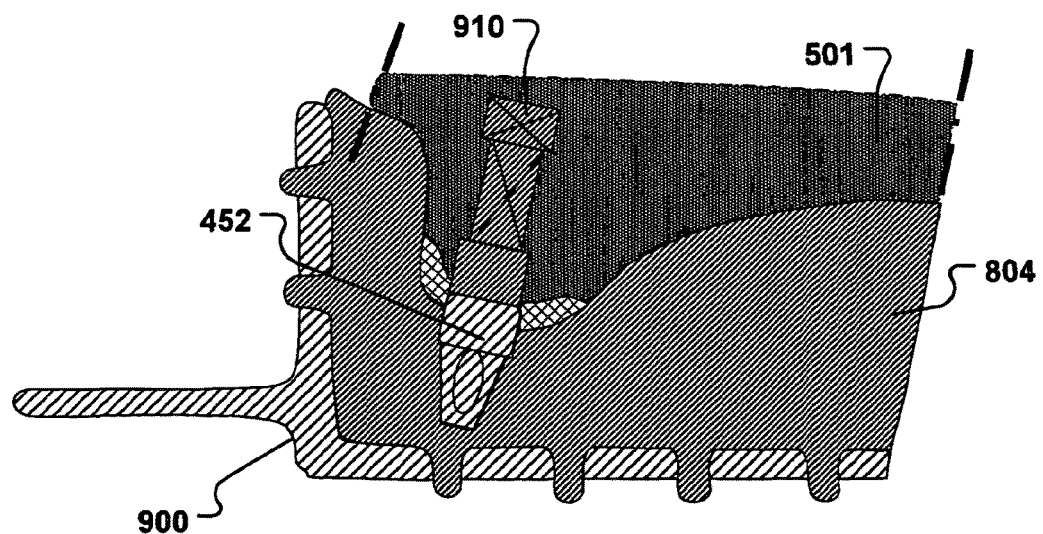

In FIGS. 13A and 13B a first model based casting alternative is shown. In laboratory work, an implant replica 910 can be mounted in the recess of the cured impression material 804 having a shape corresponding to the outer shape of the impression coping 452 shown in FIG. 11C. The implant replica 910 is mounted in an impression coping 452 situated with the well defined orientation and position in the impression material 804 contained in the impression tray 900. Further, soft tissue replica material 920 can be applied. Soft tissue material may be applied if desired. The assembly can then be filled with casting material 501, e.g., gypsum, which when cured, corresponds to the factual anatomical situation in the oral cavity. The model comprising the cured casting material 501 and the implant replica 910, the soft tissue replica 920 and the impression coping 452, can then be removed from the impression tray 900, and suitably digitized to provide scan data for the factual situation, as illustrated in FIGS. 14A, 14B.

In FIGS. 13C to 13E, a second model based casting alternative is shown, based on a try-in prosthesis 800. In laboratory work an implant replica 910 can be mounted in the recess of the cured impression material 804 having a shape corresponding to the outer shape of the impression coping 452 shown in FIGS. 11A and 11B. An implant replica 910 can be mounted in an impression coping 452 situated with the well defined orientation and position in the impression material 804 contained in the try-in prosthesis 800. Further, soft tissue replica material 920 can be applied. As illustrated in FIG. 13D, the assembly can then be filled with casting material 501, e.g., gypsum, which when cured, corresponds to the factual anatomical situation in the oral cavity. The model comprising the cured casting material 501 and the implant replica 910, the soft tissue replica 920 and the impression coping 452, can then be removed from the try-in prosthesis 800, and suitably digitized to provide scan data for the factual situation, as illustrated in FIGS. 14A, 14B. Hence, impression data based on the recess 802 can be provided for determining a factual position and orientation of the dental implant 450.

As shown in FIG. 13E, the bite index 808 may conveniently be used in an articulator to ensure a proper occlusion.

Figure 14A:
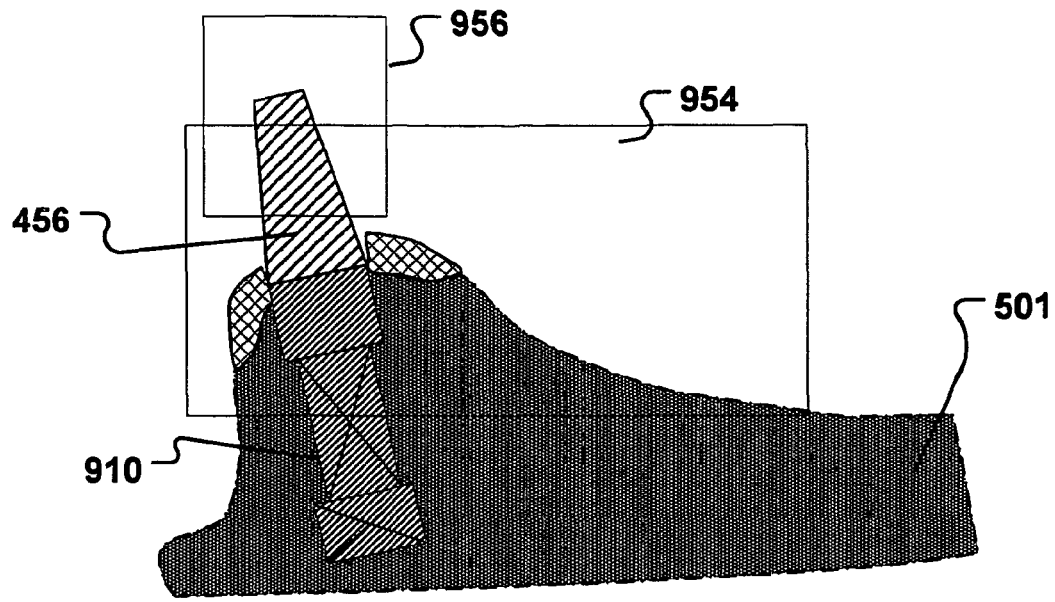
FIGS. 14A and 14B are diagrams of cross sectional views illustrating examples of scanning of a modified try-in prosthesis and of an implant position.
Figure 14B:
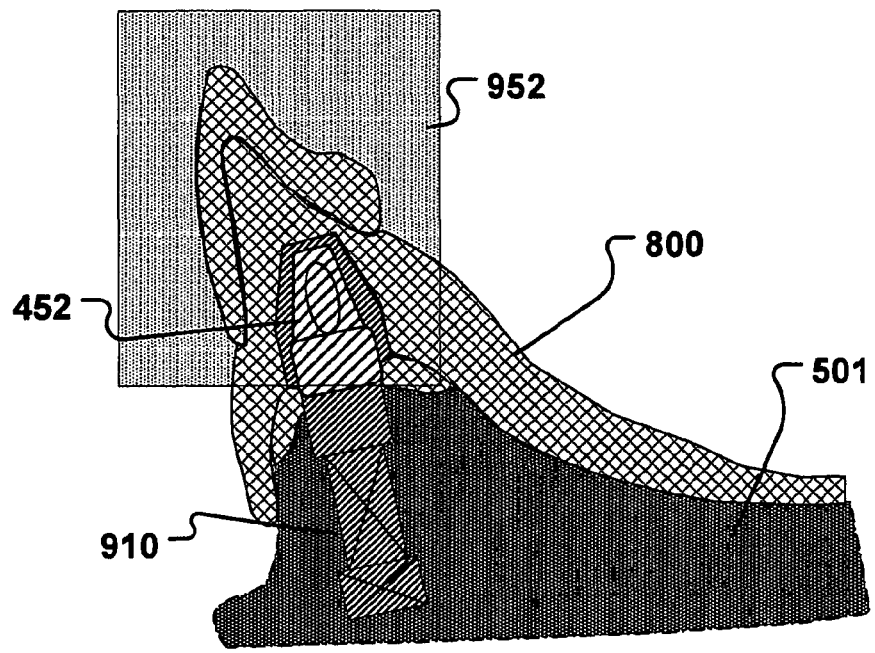

In FIGS. 14A and 14B example scanning for generation of scan data is illustrated.

In FIG. 14A soft tissue and implant positions data can be generated. This can typically be made by surface scanning. In FIG. 14A scanning of an implant position with an attached scanning implant locator 456 and a soft tissue surface is illustrated by scanning areas 954, 956. First, the soft tissue portion can be scanned, as illustrated by scan area 954. Then the implant position is provided by scanning the dental implant with the implant locator 456 affixed thereto, as illustrated by the second scan area 956. This registered data can be matched with already existing data present in the virtual planning, which can provide for the factual position data of the dental implant in relation to, such as in the same coordinate system, the planned first dental prosthesis.

Then the position locator 456 can be removed and replaced by the impression coping 452, and the modified try-in prosthesis 800 can be put on. Scanning of the adjusted (see FIG. 10B) try in prosthesis 800 is illustrated in FIG. 14B. The try in prosthesis 800 can be assembled with the model cast 501 and has the implant replica 910 contained therein. The adjusted assembly of the try in prosthesis 800 is scanned by suitable scanning techniques, e.g., volumetric scanning, such as CT scanning, or surface scanning, such as touch probe based scanning, or optical scanning, etc., as illustrated by scanning area 952. The outer surface of the modified try-in prosthesis is scanned, thus providing for the factual shape data. Again, this registered data is matched with already existing data present in the virtual planning, which provides for the factual shape data in relation to, such as in the same coordinate system, the planned first dental prosthesis.

An interior surface of said first dental restoration, such as a digitized soft tissue surface, may correspond to an interior surface of said second dental restoration. At least said second dental restoration may be a soft-tissue supported prosthesis. The soft tissue supported prosthesis may comprise a loose prosthesis, such as a temporary prosthesis, or a final soft-tissue supported prosthesis. In some embodiments, the first dental restoration and/or the second dental restoration does thus not comprise a dental implant. Consequently, dental prosthesis 800 may not have a recess 802 in such embodiments (not shown). The outer surface may thus at least partly be based on said scan data comprising a produced try-in prosthesis as the first dental prosthesis 800. The try-in prosthesis 800 is, e.g., printed by means of a rapid prototyping 3D printer. Then the try-in prosthesis can be modified and adapted to the factual patient situation, see e.g., FIG. 10B. The try-in prosthesis can then be re-scanned for providing scan data comprising factual position data and/or factual shape data based on at least a portion of the modified try-in prosthesis. Virtually planning of the second dental restoration for the patient can then be based on this scan data. The first dental restoration can be adapted to the factual patient situation as comprised in the scan data. Providing second production data based on the planned second dental restoration may then be used for production of the second dental restoration taking into respect the factual patient situation.

The scan data thus can comprise implant restoration position data for an actual position and orientation of the at least one dental implant as the factual position data, and/or dental restoration shape data for the first dental restoration as the factual shape data.

The scan data can be provided from at least a portion of the first dental restoration when installed in the oral cavity.

The scan data may be of a connection interface at a coronal end of the dental implant when installed in jaw bone tissue of the patient.

Virtually planning 16 (FIG. 1) the example second dental restoration for the patient is illustrated in FIGS. 15A-C illustrating an embodiment of updating a previously planned virtual bridge framework planning.

Starting with the first dental restoration as shown in FIG. 7B, the virtual planning can be continued, now having the scan data of the factual position data and/or shape data available. In FIG. 15A an update of the bridge framework planning with the factual position is shown. The planned implant position 610 as present in the virtual planning environment from planning the first dental restoration, can be updated with the scan data, making available a registered position 620 thereof after surgery.

In FIG. 15B, the update of the teeth geometry is illustrated. The planned teeth set up 660 can be adjusted based on the factual implant position 620 to an adjusted teeth geometry 670. The adjusted teeth geometry 670 can be input to a bridge framework update as illustrated in FIG. 15C. The initially planned bridge framework 651 of the first dental restoration can be adjusted to an updated bridge framework geometry 652 of the second dental restoration. The connection interface between the bridge framework 651 and the dental implant at position 620 can be updated and adapted to each other. The bridge framework 651 can be adjusted based on the adjusted teeth 670, such as to provide sufficient space for veneering.

An updated connection interface 655 between the bridge framework and the implant interface can be based on the registered factual implant position after surgery, wherein the connection interface of the bridge framework 651 can be adapted accordingly based on the scan data. The updated geometry of the connection interface 655 can be made to fit the actual implant position in the patient.

The updated bridge framework geometry, or other design parameters of the second dental restoration, may in addition be chosen to fulfill other criteria, such as to maintain aesthetic criteria, e.g., that enough veneering thickness is provided for, or structural strength criteria. A robust design may be provided by methods as disclosed in WO2009/033677 of the same applicant as the present application, which is incorporated herein by reference in its entirety for all purposes.

Adjusting the planned first dental restoration can be made in dependence of the scan data, and can comprise adjusting the planned first dental restoration in relation to fixed positions of the scan data. In more detail, the adjusting of said planned first dental restoration can comprise adapting said planned first dental restoration in dependence of said factual position data. The factual position of at least a portion of the planned first dental restoration can have changed, compared to the planned first dental restoration. This can comprise, for instance, adapting the position for a connection interface in said second dental restoration based on said factual position data. The dental implant may have a different position compared to the initially planned position. This factual position can be registered and used as a basis for continued planning of a second dental restoration. In the example, a position of a connection interface comprised in the planned first dental restoration can be adjusted to the factual position of the connection interface of the dental implant.

Alternatively or in addition, the adjusting of said planned first dental restoration can comprise adjusting an exterior surface, such as a shape thereof, of said first dental restoration by adapting to a shape defined by said factual shape data. This may comprise a shape of a modified first dental restoration, such as a modified dental prosthesis, e.g., to a desired smile line, etc.

A planned position and/or shape of a portion of the second dental restoration can be thus adapted to a factual position during continued virtual planning, based on the factual position data. For instance, a planned first CAD object of the first dental restoration can be compared with the same object as comprised in the scan data. To this end, the two objects can be matched, and differences observed. Where the objects differ, the planned object is adapted to the object as given by the scan data. The first planned dental prosthesis is thus adapted to the factual situation of the patient. Adaption may, e.g., be altering the position of CAD objects, such as a connection interface of the dental prosthesis to be seated on a corresponding connection interface of a dental implant.

Providing scan data can be made from at least a portion of the modified first dental restoration, and wherein the adjusting can be at least partly based on a factual position and/or shape of at least a portion of the scan data. For instance, a connection interface of the dental implant towards a bridge framework of the first dental restoration can be locked when adjusting the planned first dental restoration towards the second dental restoration.

Adjusting the planned first dental restoration may comprise adjusting a bridge framework and/or adjusting at least one virtual tooth of the planned first dental restoration, as described above.

Adjusting the planned first dental restoration may comprise adjusting a bridge framework in relation to a connection interface of the dental implant, and/or a locked coronal tooth portion, as described above.

In certain embodiments, adjusting the planned first dental restoration may only be made when the fit of the first dental restoration is in non-conformity with the planned first dental restoration.

Second production data may now be provided based on the virtually planned second dental restoration for production thereof or of products related thereto.

The first and/or second production data may be used in a method of production of a dental restoration having a desired fit or a product related to a medical procedure for installing the dental restoration in a patient. The production method can comprise receiving production data from the computer-based method of virtually planning. The method further can comprise producing the first dental restoration or the product related to a medical procedure for installing at least a portion of the first dental restoration based on the first production data. The method may further comprise producing the second dental restoration based on the second production data.

The method can be implemented in embodiments in a computer-based system for virtually planning a dental restoration for a patient. The system can comprise a processing unit adapted to virtually plan a first dental restoration for the patient; can prove first production data based on the planned first dental restoration useful for production of the first dental restoration and/or at least one product related to a medical procedure for installing at least a portion of the first dental restoration in an oral cavity of the patient; can provide scan data comprising factual position data and/or factual shape data based on the first dental restoration when at least partly installed in the oral cavity of the patient; can virtually plan a second dental restoration for the patient, comprising adjusting the planned first dental restoration in dependence of the scan data, and can provide second production data based on the planned second dental restoration useful for production of the second dental restoration.

Figure 2:
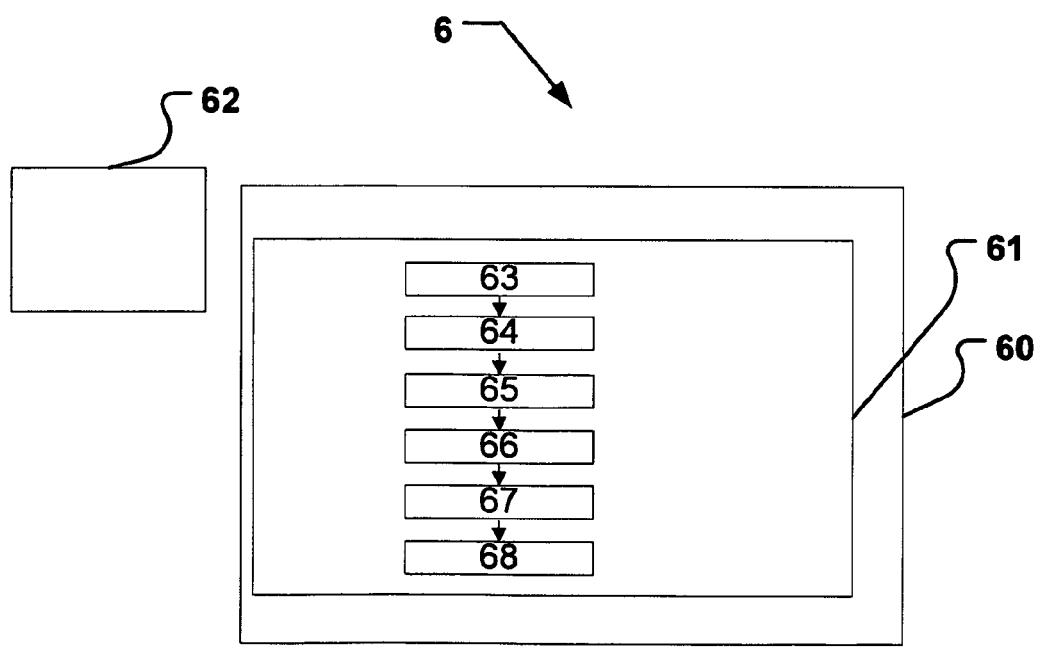
FIG. 2 is an example schematic illustration of a computer program and system.

FIG. 2 is a schematic illustration of an example computer program 61 and system 6 for implementing the method 1.

In accordance with FIG. 2, in certain embodiments, the method can be implemented in a computer program 61 for virtually planning a dental restoration in a patient, for processing by a computer 62. The computer program may be stored on a computer readable medium 60 and can comprise a plurality of code segments for virtually planning 63 a first dental restoration for the patient; providing 64 first production data based on the planned first dental restoration useful for production of the first dental restoration and/or at least one product related to a medical procedure for installing at least a portion of the first dental restoration in an oral cavity of the patient; providing 65 scan data comprising factual position data and/or factual shape data based on the first dental restoration when at least partly installed in the oral cavity of the patient; virtually planning 66 a second dental restoration for the patient, comprising adjusting the planned first dental restoration in dependence of the scan data, and providing 67 second production data based on the planned second dental restoration useful for production of the second dental restoration.

Output data from the code segment 67 may provide production data in a code segment 68 for production of elements related to the second dental restoration for implementing the virtually planned dental design in a real dental restoration.

The table below illustrated how the method may be implemented, in certain embodiments, in a distributed environment.

| Activity | Laboratory | Virtual Planning | Clinical | Production |
| --- | --- | --- | --- | --- |
| First Impression taking | | | X | |
| Production of model and wax plate | X | | | |
| Scan patient and prepared wax plate (CT), wax plate and model (optical) | X | | X | |
| Matching 3d objects | | X | | |
| Treatment planning | | X | | |
| Production of first planned products | | | | X |
| Surgery and registration of actual implant position and prosthesis adjustment | | | X | |
| Production of implant model and rescan implant position and adjusted prosthesis | X | | | |
| Update planning | | X | | |
| Production of final bridge framework | | | | X |

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

What is claimed is:

1. A method of planning a dental restoration for a patient, said method comprising:
    virtually planning a first model, via a computer, of a first dental restoration for said patient, the first dental restoration being a temporary or try-in soft tissue supported dental restoration that does not extend into bone in a virtual model of the patient, wherein the virtual planning of said first model of said first dental restoration comprises planning of a position of an implant, wherein said try-in soft tissue supported dental restoration comprises a recess, which is planned to receive the coronal portion of said implant and an impression coping or a healing cap if attached to the coronal portion of said implant when positioning said try-in dental restoration in the oral cavity of said patient when said implant is implanted therein and wherein said recess is configured to accommodate impression material for registering a position and orientation of said implant as well as of said impression coping or healing cap;
    providing first production data based on said virtually planned first model of said first dental restoration useful for production of said first dental restoration for installing said first dental restoration in an oral cavity of said patient, wherein said first dental restoration includes at least a tooth;

requesting production of said first dental restoration based on said first production data to manufacture a produced first dental restoration;

obtaining said produced first dental restoration;

installing said obtained and produced first dental restoration in said patient;

providing scan data comprising factual position data and/or factual shape data, including a factual position of said implant based on at least a portion of the installed first dental restoration resulting from installing said first dental restoration in the oral cavity of the patient after modification thereof, wherein said installed first dental restoration was produced by using said first production data and wherein said scan data on said factual position of said implant is obtained from the position and orientation of said implant as registered in said impression material in said recess of said try-in dental restoration;

virtually planning a second model, via a computer, of a second dental restoration for said patient, comprising virtually adjusting said virtually planned first dental restoration in dependence on said scan data, the second dental restoration being an implant supported dental restoration, wherein the virtually adjusting is based on an actual implant position in the patient; and providing second production data based on said virtually planned second model of said second dental restoration useful for production of said second dental restoration, wherein the first dental restoration in its entirety is discarded or not used upon installation of the second dental restoration in the oral cavity of said patient.

2. The method of claim 1, wherein virtually planning said first dental restoration comprises virtually planning at least one of a soft-tissue supported prosthesis;
   a temporary prosthesis;
   a try-in prosthesis; or
   the position of at least one dental implant wherein said first production data comprises data for a surgical template for installing said at least one dental implant in said patient.

3. The method of claim 2, wherein said scan data comprises shape data of an exterior surface of said modified first dental restoration as said factual shape data.

4. The method of claim 2, wherein said first production data comprises data for a try-in prosthesis devised to be positioned in an oral cavity of the patient.

5. The method of claim 2, wherein said virtually adjusting said virtually planned first dental restoration comprises virtually adjusting a virtual bridge framework in relation to a connection interface of said dental implant.

6. The method of claim 1, wherein providing first production data is based on said virtually planned first model of said first dental restoration and at least one product related to a medical procedure for installing said first dental restoration in an oral cavity of said patient, and wherein said at least one product related to said medical procedure is a surgical template for drill guided dental surgery, or a try-in restoration.

7. The method of claim 1, wherein said virtually adjusting said virtually planned first dental restoration comprises adapting said virtually planned first dental restoration in dependence of said factual position data.

8. The method of claim 7, wherein adapting said planned first dental restoration in dependence of said factual position data comprises adapting a position for a connection interface in said second dental restoration based on said factual position data and/or adjusting an exterior surface of said first dental restoration by adapting to a shape defined by said factual shape data.

9. The method of claim 1, wherein said virtually adjusting said virtually planned first dental restoration comprises virtually adjusting a virtual bridge framework and/or virtually adjusting at least one virtual tooth of said virtually planned first dental restoration.

10. The method of claim 1, wherein an interior surface of said first dental restoration corresponds to an interior surface of said second dental restoration.

11. The method of claim 10, wherein the interior surface of said first dental restoration comprises a digitized soft tissue surface.

12. The method of claim 1, wherein the first dental restoration is not an implant.

13. The method of claim 1, wherein virtually planning the first model includes modifying the first model for a position of a recess based on the position of the implant.

14. The method of claim 1, wherein the factual position of the implant is registered as a basis for the virtual adjusting.

15. A method of production of a dental restoration, comprising:
   a) performing the method according to claim 1;
   b) receiving said first production data and said second production data; and
   c) at least one of: (i) producing said first dental restoration or a product related to a medical procedure for installing said first dental restoration based on said first production data, and (ii) producing said second dental restoration based on said second production data.

16. A computer-based system for planning a dental restoration for a patient, said system comprising a processor adapted to virtually plan a first model of a first dental restoration for said patient, the first dental restoration being a temporary or try-in soft tissue supported dental restoration that does not extend into bone in a virtual model of the patient, wherein the virtual planning of said first model of said first dental restoration comprises planning of a position of an implant, wherein said try-in soft tissue supported dental restoration comprises a recess, which is planned to receive the coronal portion of said implant and an impression coping or a healing cap if attached to the coronal portion of said implant when positioning said try-in dental restoration in the oral cavity of said patient when said implant is implanted therein and wherein said recess is configured to accommodate impression material for registering a position and orientation of said implant as well as of said impression coping or healing cap;

provide first production data based on said virtually planned first model of said first dental restoration useful for production of said first dental restoration for installing said first dental restoration in an oral cavity of said patient, wherein said first dental restoration includes at least a tooth;

use said first production data to request production of said first dental restoration;

request production of said first dental restoration based on said first production data to manufacture a produced first dental restoration;

provide scan data comprising factual position data and/or factual shape data, including a factual position of said implant based on said produced first dental restoration when installed in said oral cavity of said patient and wherein said scan data on said factual position of said implant is obtained from the position and orientation of said implant as registered in said impression material in said recess of said try-in dental restoration;

virtually plan a second model of a second dental restoration for said patient, comprising virtually adjusting said virtually planned first dental restoration in dependence of said scan data, the second dental restoration being an implant supported dental restoration, wherein the virtually adjusting is based on an actual implant position in the patient; and provide second production data based on said virtually planned second model of said second dental restoration useful for production of said second dental restoration, wherein the first dental restoration in its entirety is discarded or not used upon installation of the second dental restoration in said oral cavity of said patient.

17. The system of claim 16, wherein virtually planning the first model includes modifying the first model for a position of a recess based on the position of the implant.

18. The system of claim 16, wherein the factual position of the implant is registered as a basis for the virtual adjusting.

19. A non-transitory computer readable medium containing a plurality of code segments for planning a dental restoration in a patient, wherein execution of the plurality of code segments by a computer carries out a method, comprising:

virtually planning a first model of a first dental restoration for said patient, the first dental restoration being a temporary or try-in soft tissue supported dental restoration that does not extend into bone in a virtual model of the patient, wherein the virtual planning of said first model of said first dental restoration comprises planning of a position of at least one implant;

providing first production data based on said virtually planned first model of said first dental restoration useful for production of said first dental restoration for installing said first dental restoration in an oral cavity of said patient, wherein said first dental restoration includes at least a tooth;

using said first production data for requesting production of said first dental restoration;

requesting production of said first dental restoration based on said first production data to manufacture a produced first dental restoration;

providing scan data comprising factual position data and/or factual shape data, including a factual position of said implant based on said produced first dental restoration when installed in said oral cavity of said patient and wherein said scan data on said factual position of said implant is obtained from a position and orientation of said implant as registered in impression material in a recess of said try-in dental restoration;

virtually planning a second model of a second dental restoration for said patient, comprising virtually adjusting said virtually planned first dental restoration in dependence of said scan data, the second dental restoration being an implant supported dental restoration, wherein the virtually adjusting is based on an actual implant position in the patient; and providing second production data based on said virtually planned second model of said second dental restoration useful for production of said second dental restoration, wherein the first dental restoration in its entirety is discarded or not used upon installation of the second dental restoration in said oral cavity of said patient.

* * * * *